(12) United States Patent
Schroff et al.

(10) Patent No.: US 11,578,331 B2
(45) Date of Patent: *Feb. 14, 2023

(54) COMBINATION COMPRISING IMMUNOSTIMULATORY OLIGONUCLEOTIDES

(71) Applicant: Gilead Sciences, Inc., Foster City, CA (US)

(72) Inventors: Matthias Schroff, Berlin (DE); Manuel Schmidt, Berlin (DE); Kerstin Kapp, Berlin (DE); Alfredo Zurlo, Berlin (DE)

(73) Assignee: Gilead Sciences, Inc., Foster City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/793,334

(22) Filed: Feb. 18, 2020

(65) Prior Publication Data

US 2021/0010003 A1   Jan. 14, 2021

Related U.S. Application Data

(60) Continuation of application No. 16/450,324, filed on Jun. 26, 2019, now Pat. No. 10,604,760, which is a division of application No. 15/756,798, filed as application No. PCT/EP2016/071314 on Sep. 9, 2016, now Pat. No. 10,487,333.

(30) Foreign Application Priority Data

Sep. 9, 2015   (LU) .......................................... 92821

(51) Int. Cl.
| | |
|---|---|
| *C12N 15/117* | (2010.01) |
| *C12N 15/11* | (2006.01) |
| *C07K 16/30* | (2006.01) |
| *C07K 16/28* | (2006.01) |
| *A61K 39/395* | (2006.01) |
| *A61P 35/00* | (2006.01) |
| *A61K 31/7088* | (2006.01) |
| *A61K 39/00* | (2006.01) |

(52) U.S. Cl.
CPC ........ *C12N 15/117* (2013.01); *A61K 31/7088* (2013.01); *A61K 39/3955* (2013.01); *A61K 39/39541* (2013.01); *A61P 35/00* (2018.01); *C07K 16/2818* (2013.01); *C07K 16/2827* (2013.01); *C07K 16/30* (2013.01); *C12N 15/111* (2013.01); *A61K 2039/505* (2013.01); *C12N 2310/17* (2013.01); *C12N 2310/32* (2013.01); *C12N 2310/344* (2013.01); *C12N 2310/531* (2013.01); *C12N 2310/532* (2013.01); *C12N 2320/31* (2013.01)

(58) Field of Classification Search
CPC ...... A61K 39/3955; A61P 35/00; A61P 37/00; C12N 15/111; C12N 15/117; C12N 2310/17

USPC ..................... 435/6.1, 91.1, 91.31, 455, 458; 514/44 A; 536/23.1, 24.5
See application file for complete search history.

(56) References Cited

U.S. PATENT DOCUMENTS

| | | |
|---|---|---|
| 2,382,696 A | 8/1945 | De |
| 2,699,718 A | 1/1955 | Wright |
| 4,363,649 A | 12/1982 | Yamato et al. |
| 5,663,153 A | 9/1997 | Hutcherson et al. |
| 5,723,335 A | 3/1998 | Hutcherson et al. |
| 5,750,669 A | 5/1998 | Roesch et al. |
| 5,856,462 A | 1/1999 | Agrawal |
| 6,251,666 B1 | 6/2001 | Beigelman |
| 6,449,725 B2 | 9/2002 | Deenadhayalan et al. |
| 6,589,940 B1 | 7/2003 | Raz et al. |
| 6,737,066 B1 | 5/2004 | Moss |
| 6,849,725 B2 | 2/2005 | Junghans |
| 6,849,726 B2 | 2/2005 | Usman et al. |
| 6,977,245 B2 | 12/2005 | Klinman et al. |
| 7,378,509 B2 | 5/2008 | Mcevoy et al. |
| 7,501,503 B2 | 3/2009 | Damha et al. |
| 7,517,862 B2 | 4/2009 | Agrawal et al. |
| 7,635,468 B2 | 12/2009 | Dobric et al. |
| 7,674,777 B2 | 3/2010 | Krieg et al. |
| 7,879,992 B2 | 2/2011 | Vickers et al. |
| 8,017,591 B2 | 9/2011 | Brzezicha et al. |
| 9,212,366 B2 | 12/2015 | Wittig et al. |
| 9,345,754 B2 | 5/2016 | Dobric et al. |
| 9,422,564 B2 | 8/2016 | Dina et al. |
| 9,499,815 B1 | 11/2016 | Schroff |

(Continued)

FOREIGN PATENT DOCUMENTS

| | | |
|---|---|---|
| DE | 10211558 A1 | 10/2003 |
| EP | 0855184 A1 | 7/1998 |

(Continued)

OTHER PUBLICATIONS

Communication issued by the Indian Patent Office in counterpart Indian Patent Application No. 6051/DELNP/2013, dated Nov. 9, 2017.

(Continued)

*Primary Examiner* — Jane J Zara

(74) *Attorney, Agent, or Firm* — Mintz, Levin, Cohn, Ferris, Glovsky and Popeo, P.C.

(57) ABSTRACT

The invention relates to a combination and its use for the treatment of diseases. The instant disclosure provides a combination of a so-called T-cell regulator selected from the group comprising PD1, PD-L1, OX40, TIM-3, LAG3, CD137(4-1BB) and a non-coding immunomodulating DNA.

4 Claims, 13 Drawing Sheets

Specification includes a Sequence Listing.

(56) References Cited

U.S. PATENT DOCUMENTS

| | | | |
|---|---|---|---|
| 10,006,032 B2 | 6/2018 | Schroff et al. | |
| 10,487,333 B2 | 11/2019 | Schroff et al. | |
| 10,604,760 B2* | 3/2020 | Schroff | A61P 35/00 |
| 2002/0095033 A1 | 7/2002 | Ramasamy et al. | |
| 2003/0050263 A1 | 3/2003 | Krieg et al. | |
| 2003/0125279 A1 | 7/2003 | Junghans et al. | |
| 2006/0183703 A1 | 8/2006 | Schroff et al. | |
| 2006/0241076 A1 | 10/2006 | Uhlmann et al. | |
| 2007/0049546 A1 | 3/2007 | Brzezicha et al. | |
| 2007/0142315 A1 | 6/2007 | Forsbach et al. | |
| 2007/0179101 A1 | 8/2007 | Kitagawa et al. | |
| 2008/0131466 A1 | 6/2008 | Reed et al. | |
| 2008/0260820 A1 | 10/2008 | Borrelly et al. | |
| 2008/0311630 A1 | 12/2008 | Schroff et al. | |
| 2009/0004703 A1 | 1/2009 | Schroff | |
| 2009/0082295 A1 | 3/2009 | Jungnelius et al. | |
| 2009/0136528 A1 | 5/2009 | Singh et al. | |
| 2009/0169472 A1 | 7/2009 | Diebold et al. | |
| 2009/0181078 A1 | 7/2009 | Reed et al. | |
| 2010/0130593 A1 | 5/2010 | Garren et al. | |
| 2010/0303803 A1 | 12/2010 | Schroff et al. | |
| 2011/0098456 A1 | 4/2011 | Uhlmann et al. | |
| 2014/0010830 A1 | 1/2014 | Schroff et al. | |
| 2018/0251767 A1 | 9/2018 | Schroff et al. | |
| 2019/0316134 A1 | 8/2019 | Schroff et al. | |
| 2020/0230234 A1 | 7/2020 | Schroff et al. | |
| 2021/0010003 A1 | 1/2021 | Schroff et al. | |
| 2021/0340543 A1 | 11/2021 | Schroff et al. | |

FOREIGN PATENT DOCUMENTS

| | | |
|---|---|---|
| EP | 0941318 A1 | 9/1999 |
| EP | 1196178 B1 | 6/2004 |
| EP | 1776124 A1 | 4/2007 |
| EP | 2246433 A1 | 11/2010 |
| EP | 2333091 A2 | 6/2011 |
| EP | 2197488 B1 | 5/2014 |
| EP | 2655623 B1 | 2/2017 |
| EP | 2999787 B1 | 4/2017 |
| FR | 1418965 A | 11/1965 |
| FR | 2732971 A1 | 10/1996 |
| GB | 191115253 A | 6/1912 |
| GB | 684057 A | 12/1952 |
| GB | 2523187 A | 8/2015 |
| JP | 2002503212 A | 1/2002 |
| JP | 2003204793 A | 7/2003 |
| JP | 2012157312 A | 2/2011 |
| RU | 2351362 C2 | 4/2009 |
| WO | 9818810 A1 | 5/1998 |
| WO | 9821322 A1 | 5/1998 |
| WO | 0050075 A2 | 8/2000 |
| WO | 0100232 A2 | 1/2001 |
| WO | 0107055 A1 | 2/2001 |
| WO | 0140515 A1 | 6/2001 |
| WO | 0226757 A2 | 4/2002 |
| WO | 02060476 A2 | 8/2002 |
| WO | 03004602 A2 | 1/2003 |
| WO | 03031469 A2 | 4/2003 |
| WO | 03031470 A2 | 4/2003 |
| WO | 03057822 A2 | 7/2003 |
| WO | 2004041183 A2 | 5/2004 |
| WO | 2005042018 A2 | 5/2005 |
| WO | 2005063280 A1 | 7/2005 |
| WO | 2005080567 A1 | 9/2005 |
| WO | 2006002038 A2 | 1/2006 |
| WO | 2006015872 A1 | 2/2006 |
| WO | 2006091591 A1 | 8/2006 |
| WO | 2007089871 A2 | 1/2007 |
| WO | 2007047396 A2 | 4/2007 |
| WO | 2007/131495 A2 | 11/2007 |
| WO | 2008153733 A2 | 12/2008 |
| WO | 2009035554 A2 | 3/2009 |
| WO | 2009059805 A1 | 5/2009 |
| WO | 2009069447 A1 | 6/2009 |
| WO | 2009069682 A1 | 6/2009 |
| WO | 2010039137 A1 | 4/2010 |
| WO | 2010125182 A1 | 11/2010 |
| WO | 2011117408 A1 | 9/2011 |
| WO | 2012085282 A1 | 6/2012 |
| WO | 2012085291 A1 | 6/2012 |
| WO | 2014191222 A1 | 12/2014 |
| WO | 2015/124614 A1 | 8/2015 |
| WO | 2017042336 A1 | 3/2017 |
| WO | 2017050806 A1 | 3/2017 |
| WO | 2018193137 A1 | 10/2018 |
| WO | 2019043192 A1 | 3/2019 |
| WO | 2019043194 A1 | 3/2019 |

OTHER PUBLICATIONS

European Patent Office Search Report for EP1647518A1 and English translation thereof, dated Jan. 20, 2006, 2 pages.
GB1516676.2 United Kingdom Search Report, dated Jul. 7, 2016, 2 pages.
International Preliminary Report on Patentability received for International Application No. PCT/EP2011/074033, dated Jul. 4, 2013, 7 pages.
International Preliminary Report on Patentability received for International Application No. PCT/EP2016/071314, dated Mar. 22, 2018, 11 pages.
International Preliminary Report on Patentability received for International Application No. PCT/EP2016/072385, dated Apr. 5, 2018, 9 pages.
International Search Report and Written Opinion received for Patent International Application No. PCT/EP2011/074033, dated Mar. 27, 2012, 10 pages.
International SeaOrch Report and Written Opinion received for International Application No. PCT/EP2016/071314, dated Feb. 16, 2017, 17 pages.
Wikibooks, "Structural Biochemistry/Organic Chemistry/Carbohydrates" Wikibooks entry, Apr. 30, 2018, retrieved from https://en.wikibooks.org/w/index.php?title=Structural_Biochemistry/Organic_Chemistry/Carbohydrates&oldid=3176675.
Aggarwal et al., "Augmentation of HIV-1 Subtype C Vaccine Constructs Induced Immune Response in Mice by CpG Motif 1826-ODN", Viral Immunology, Mar. 31, 2005, 18(1):213-223.
Agrawal et al., "Antisense Therapeutics: is it as Simple as Complementary Base Recognition?", Molecular Medicine Today, Mar. 2000, 6(2):72-81.
Archin et al., "Administration of Vorinostat Disrupts HIV-1 Latency in Patients on Antiretroviral Therapy", Nature, 2012, 487(7408):482-485.
Ayash-Rashkovsky et al., "Generation of Th1 Immune Responses to Inactivated, gp120-depleted HIV-1 in Mice with a Dominant Th2 Biased Immune Profile Via Immunostimulatory Oligonucleotides-relevance to AIDS Vaccines in Developing Countries", Vaccine, Jun. 21, 2002, 20(21-22):2684-2692.
Bailey et al., "Mechanisms of HIV-1 Escape from Immune Responses and Antiretroviral Drugs", Current Opinion in Immunology, Aug. 2004, 16(4):470-476.
Blommers et al., "Effects of the Introduction of L-nucleotides into DNA. Solution Structure of the Heterochiral Duplex d(G-C-G-(L)T-G-C-G).d(C-G-C-A-C-G-C) Studied by NMR Spectroscopy", Biochemistry, Jun. 28, 1994, 33(25):7886-7896.
Brassard et al., "Interferon-α as an Immunotherapeutic Protein", Journal of Leukocyte Biology, Apr. 2002, 71(4):565-581.
Brown et al., "Effect of Phosphorothioate Modification of Oligodeoxynucleotides on Specific Protein Binding", Journal of Biological Chemistry, Oct. 28, 1994, 269(43):26801-26805.
Chen et al. (1992) "Generation and Analysis of Random Point Mutations in an Antibody CDR2 Sequence: Many Mutated Antibodies Lose their Ability to Bind Antigen", Journal of Experimental Medicine, 176(3):855-866.
Clinicaltrials.gov, "Toll-like Receptor 9 Agonist Treatment in Chronic HIV-1 Infection (TEACH)", ClinicalTrials.gov, website, May 13, 2015, Trial No. NCT02443935, 3 pages.

(56) References Cited

OTHER PUBLICATIONS

Clinicaltrials.gov, "Toll-like Receptor 9 Enhancement of Antiviral Immunity in Chronic HIV-1 Infection: A Phase 1 b/2a Trial (Teach)", EU Clinical Trials Register, Apr. 7, 2015, EudraCT No. 2014-005634-59, 6 pages.

Clusel et al., "Ex Vivo Regulation of Specific Gene Expression by Nanomolar Concentration of Double-stranded Dumbbell Oligonucleotides", Nucleic Acids Research, 1993, 21(15):3405-3411.

Damha et al., "Antisense L/D-Oligodeoxynucleotide Chimeras: Nuclease Stability, Base-Pairing Properties, and Activity at Directing Ribonuclease H", Biochemistry, 1994, 33(25):7877-7885.

Doi et al., "Structural Characteristics of Enantiomorphic DNA: Crystal Analysis of Racemates of the d(CGCGCG) Duplex", Journal of the American Chemical Society, 1993, 115(22):10432-10433.

Erie et al., "A Dumbbell-shaped, Double-hairpin Structure of DNA: A Thermodynamic Investigation", Biochemistry, Nov. 1, 1987, 26(22):7150-7159.

Fraser et al., "The Serum Mannose-binding Protein and the Macrophage Mannose Receptor are Pattern Recognition Molecules that Link Innate and Adaptive Immunity", Seminars in Immunology, Oct. 1998, 10(5):363-372.

Garbesi et al., "L-DNAs as Potential Antimessenger Oligonucleotides: A Reassessment", Nucleic Acids Research, 1993, 21(18):4159-4165.

Gonzalo et al., "A Heterologous Prime-boost Regime using DNA and Recombinant Vaccinia Virus Expressing the Leishmania Infantum P36/LACK Antigen Protects BALB/c Mice from Cutaneous Leishmaniasis", Vaccine, Jan. 15, 2002, 20(7-8):1226-1231.

Goodchild John, "Conjugates of Oligonucleotides and Modified Oligonucleotides: A Review of their Synthesis and Properties", Bioconjugate Chemistry, May 1990, 1(3):165-187.

Harcourt, "Modulation of Double-stranded RNA-mediated Gene Induction by Interferon in Human Umbilical Vein Endothelial Cells", Journal of Interferon and Cytokine Research, Nov. 20000, 20(11):1007-1013.

Hauser et al., "Utilising the Left-helical Conformation of L-DNA for Analysing Different Marker Types on a Single Universal Microarray Platform", Nucleic Acids Research, 2006, 34(18):5101-5111.

Hayashi et al., "Application of L-DNA as a Molecular Tag", Nucleic Acids Symposium Series, 2005, (49):261-262.

Hayashi et al., "Detection of L-DNA-tagged PCR Products by Surface Plasmon Resonance Imaging", ChemBioChem, Jan. 22, 2007, 8(2):169-171.

Hayashi et al., "Genotyping by Allele-specific L-DNA-tagged PCR", Journal of Biotechnology, Jun. 2008, 135(2):157-160.

Heikenwalder et al., "Lymphoid Follicle Destruction and immunosuppression after Repeated CpG Oligodeoxynucleotide Administration", Nature Medicine, Feb. 2002, 10(2):187-192.

Hosono et al., "Properties of Base-pairing in the Stem Region of Hairpin Antisense Oligonucleotides Containing 2'-methoxynucleosides", Biochimica et Biophysica Acta (BBA)—General Subjects, Jun. 9, 1995, 1244(2-3):339-344.

Kapp et al., "Genuine Immunomodulation With dSLIM", Molecular Therapy-Nucleic Acids, Jun. 2014, 3(6):e170.

Kim et al., "Superior Structure Stability and Selectivity of Hairpin Nucleic Acid Probes with an L-DNA Stem", Nucleic Acids Research, Oct. 24, 2007, 35(21):7279-7287.

Köchling et al., "Protection of Mice against Philadelphia Chromosome-positive Acute Lymphoblastic Leukemia by Cell-based Vaccination Using Nonviral, Minimalistic Expression Vectors and Immunomodulatory Oligonucleotides", Clinical Cancer Research, Aug. 1, 2003, 9(8):3142-3149.

Koechling et al., "Optimization of DNA vaccine strategies protects mice against syngeneic Ph+ ALL", Blood, Nov. 16, 2003, 102/11:746a, Abstract only.

Kovarik et al., "CpG Oligodeoxynucleotides Can Circumvent the Th2 Polarization of Neonatal Responses to Vaccines But May Fail to Fully Redirect Th2 Responses Established by Neonatal Priming1", The Journal of Immunology, 1999, 162(3):1611-1617.

Krieg et al., "Causing a Commotion in the Blood: Immunotherapy Progresses From Bacteria to Bacterial DNA", Immunol Today, 2000, 21(10):521-526.

Krieg et al., "CpG motifs in bacterial DNA trigger direct B-cell activation", Nature, May 1995, 374(6522):546-549.

Krieg et al., "Oligodeoxynucleotide Modifications Determine the Magnitude of B Cell Stimulation by CpG Motifs", Antisense and Nucleic Acid Drug Development, 1996, 6(2):133-139.

Krieg et al., "P-Chirality-Dependent Immune Activation by Phosphorothioate CpG Oligodeoxynucleotides", Oligonucleotides, 2003, 13(6):491-499.

Krieg et al., "Sequence Motifs in Adenoviral DNA Block Immune Activation by Stimulatory CpG Motifs", Proceedings of the National Academy of Sciences, Oct. 1998, 95(21):12631-12636.

Krieg, Arthur M., "CpG DNA: A Pathogenic Factor in Systemic Lupus Erythematosus?", Journal of Clinical Immunology, Nov. 1995, 15(6):284-292.

Krieg, Arthur M., "CpG Motifs: The Active Ingredient in Bacterial Extracts?", Nature Medicine, Jul. 2003, 9(7):831-835.

Krieg, Arthur M., "Development of TLR9 Agonists for Cancer Therapy", The Journal of Clinical Investigation, May 2007, 117(5):1184-1194.

Krieg, Arthur M., "Therapeutic Potential of Toll-like Receptor 9 Activation", Nature Reviews Drug Discovery, Jun. 2006, 5(6):471-484.

Krishnamachari et al., "Innovative Strategies for Co-delivering Antigens and CpG oligonucleotides", Advanced Drug Delivery Reviews, Mar. 28, 2009, 61(3):205-217.

Kulkarni et al., "Costimulatory Activation of Murine Invariant Natural Killer T Cells by Toll-like Receptor Agonists", Cellular Immunology, May-Jun. 2012, 277(1-2):33-43.

Lai et al., "Comparison of D-G3139 and Its Enantiomer L-G3139 in Melanoma Cells Demonstrates Minimal In Vitro but Dramatic In Vivo Chiral Dependency", The American Society of Gene Therapy, Feb. 2007, 15(2):270-278.

Lee et al., "IL-8 Reduced Tumorigenicity of Human Ovarian Cancer In Vivo Due to Neutrophil Infiltration", The Journal of Immunology, Mar. 1, 2000, 164(5):2769-2775.

Leva et al., "GnRH Binding RNA and DNA Spiegelmers: A Novel Approach Toward GnRH Antagonism", Chemistry & Biology, Mar. 2002, 9(3):351-359.

Levin, Arthur A., "A Review of the Issues in the Pharmacokinetics and Toxicology of Phosphorothiate Antisense Oligonucleotides", Biochimica et Biophysica Acta (BBA)—Gene Structure and Expression, Dec. 10, 2009, 1489(1):69-84.

Lim et al., "Sequence-Independent Inhibition of RNA Transcription by DNA Dumbbells and Other Decoys", Nucleic Acids Research, Feb. 1997, 25(3):575-581.

Lin et al., "Mirror Image DNA Nanostructures for Chiral Supramolecular Assemblies", Nano Letters, Jan. 2009, 9(1):433-436(8 pages).

Liu et al., "Immunostimulatory CpG Oligodeoxynucleotides Enhance the Immune Response to Vaccine Strategies Involving Granulocyte-macrophage Colony-stimulating Factor", Blood, Nov. 15, 1998, 92(10):3730-3736.

Marshall et al., "Novel Chimeric Immunomodulatory Compounds Containing Short CpG Oligodeoxyribonucleotides have Differential Activities in Human Cells", Nucleic Acids Research, 2003, 31(17):5122-5133.

Mathews et al., "Excerpt from "Biochemistry" Chapter 4: Nucleic Acid", The Benjamin Cummings Publishing Company, Inc., 1990, pp. 108-111.

McCluskie et al., "Route and Method of Delivery of DNA Vaccine Influence Immune Responses in Mice and Non-Human Primates", Molecular Medicine, 1999, 5(5):287-300.

McNaught et al., "IUPAC Compendium of Chemical Terminology", 2.0 ed. (the "Gold Book"), Definition of Configuration Stereochemical, May 1997, Blackwell Scientific Publications; Oxford.

Medzhitov, Ruslan, "Toll-like Receptors and Innate Immunity", Nature Reviews Immunology, Nov. 1, 2001, 1(2):135-145.

Melief et al., "T-cell Immunotherapy of Cancer", Research in Immunology, Jun.-Aug. 1991, 142(5-6):425-429.

Miller et al., "Transduction of Human Melanoma Cell Lines with the Human Interleukin-7 Gene Using Retroviral-mediated Gene

(56) References Cited

OTHER PUBLICATIONS

Transfer: Comparison of Immunologic Properties with Interleukin-2", Blood, Dec. 1993, 82(12):3686-3694.
Moelling, K., "Naked DNA—the Poor Man's Gene Therapy?", Gene Therapy, 1998, 5(5):573-574.
Moreno et al., "Toll-like Receptor Agonists and Invariant Natural Killer T-cells Enhance Antibody-dependent Cell-mediated Cytotoxicity (ADCC)", Cancer Letters, 2008, 272(1):70-76.
Moseman et al., "Human Plasmacytoid Dendritic Cells Activated by CpG Oligodeoxynucleotides Induce the Generation of CD4+CD25+ Regulatory T Cells", The Journal of Immunology, Oct. 1, 2004, 173(7):4433-4442.
Noguchi et al., "Induction of Antitumor Immunity by Transduction of CD40 Ligand Gene and Interferon-γ Gene into Lung Cancer", Cancer Gene Therapy, 2001, 8(6):421-429.
Offersen et al., "A Novel TLR-9 Agonist (MGN1703) Activates NK-cells and Enhances NK-cell Mediated Viral Killing of HIV-1 Infected CD4+ T Cells Ex Vivo", Towards an HIV Cure Symposium, Jul. 18-19, 2015, 113 pages.
Ohno et al., "Antigen-binding Specificities of Antibodies are Primarily Determined by Seven Residues of VH", Proceedings of the National Academy of Sciences, May 1, 1985, 82(9):2945-2949.
Paillard, Florence, "The Search for the "Best" Cytokine to Induce Antitumor Immunity", Human Gene Therapy, 1998, 9(17):2457-2458.
Pasternak et al., "Chronic Myelogenous Leukemia: Molecular and Cellular Aspects", Journal of Cancer Research and Clinical Oncology, 1998, 124(12):643-660.
Pelicano et al., "Excision of Beta-D- and Beta-L-nucleotide Analogs from DNA by the Human Cytosolic 3'-to-5' Exonuclease", Molecular Pharmacology, May 2000, 57(5):1051-1055.
Perng et al., "Towards an Understanding of the Herpes Simplex Virus Type 1 Latency-Reactivation Cycle", Interdisciplinary Perspectives on Infectious Diseases, 2010, vol. 2010, Article ID 262415, 18 pages.
Purschke et al., "A DNA Spiegelmer to Staphylococcal Enterotoxin B", Nucleic Acids Research, Jun. 15, 2003, 31(12):3027-3032.
Rasmussen et al., "Comparison of HDAC Inhibitors in Clinical Development", Human Vaccines & Immunotherapeutics, May 2013, 9(5):993-1001.
Riera-Knorrenschild et al., "Maintenance with the TLR-9 Agonist MGN1703 versus Placebo in Patients with Advanced Colorectal Carcincoma (mCRC): A Randomized Phase II Trial (IMPACT)", Journal of Clinical Oncology, May 2013, 31(15_suppl):3643-3643.
Rudikoff et al., "Single Amino Acid Substitution Altering Antigen-Binding Specificity", Proceedings of the National Academy of Sciences, Mar. 1, 1982, 79(6):1979-1983.
Rutz et al., "Toll-like Receptor 9 Binds Single-stranded CpG-DNA in a Sequence- and pH-dependent Manner", European Journal of Immunology, Sep. 2004, 34(9):2541-2550.
Schakowski et al., "A Novel Minimal-Size Vector (MIDGE) Improves Transgene Expression in Colon Carcinoma Cells and Avoids Transfection of Undesired DNA", Molecular Therapy, May 2001, 3(5):793-800.
Schirmbeck et al., "Priming of Immune Responses to Hepatitis B Surface Antigen with Minimal DNA Expression Constructs Modified with a Nuclear Localization Signal Peptide", Journal of Molecular Medicine, 2001, 79(5-6):343-350.
Schmidt et al., "Combination of TLR9 Agonist Lefitolimod/MGN1703 with Checkpoint Inhibitors for Cancer Immunotherapy", Journal of Clinical Oncology, Feb. 1, 2017, 35(4):634-634.
Schmidt et al., "Cytokine and Ig-production by CG-containing Sequences with Phosphorodiester Backbone and Dumbbell-shape", Allergy, 2006, 61(1):56-63.
Schmidt et al., "Design and Structural Requirements of the Potent and Safe TLR-9 Agonistic Immunomodulator MGN1703", Nucleic Acid Therapeutics, May 19, 2015, 25(3):130-140.
Schmidt et al., "Immune-Modulatory Function of CPG Sequence Motifs in Covalently-Closed, Double-Stem-Loop DNA Constructs (dSLIM)", Blood, Nov. 16, 2003, 102(11):769a-770a.

Schmidt et al., "TLR9 agonist lefitolimod to improve antitumor effect of checkpoint inhibitors in vivo", Journal of Clinical Oncology, 2017, 35(15).
Schmoll et al., "Updated results of the randomized phase 2 impact trial: maintenance with TLR-9 agonist MGN1703 vs placebo in patients with metastatic colorectal carcinoma (MCRC)", Annals of oncology, Jun. 2013, 24(Suppl), iv16-iv17.
Seder et al., "Acquisition of lymphokine-producing phenotype by CD4+ T cells", Annual Review of Immunology, 1994, 12:635-673.
Shaffer, Anita T., "Immunotherapy Doubts Fading in GI Cancers", Apr. 26, 2016, https://www.onclive.com/view/immunotherapy-doubts-fading-in-gi-cancers, 3 pages.
Shan et al., "Stimulation of HIV-1-Specific Cytolytic T Lymphocytes Facilitates Elimination of Latent Viral Reservoir after Virus Reactivation", Immunity, Mar. 23, 2012, 36(3):491-501.
Sheehan et al., "Phosphorothioate Oligonucleotides Inhibit the Intrinsic Tenase Complex", Blood, Sep. 1, 1998, 92(5):1617-1625.
Silvera et al., "Vaccination with gp120-depleted HIV-1 Plus Immunostimulatory CpG Oligodeoxynucleotides in Incomplete Freund's Adjuvant Stimulates Cellular and Humoral Immunity in Rhesus Macaques", Vaccine,Dec. 21, 2004, 23(6):827-839.
Sin et al., "Interleukin 7 Can Enhance Antigen-Specific Cytotoxic-T-Lymphocyte and/or Th2-Type Immune Responses In Vivo", Clinical And Diagnostic Laboratory Immunology, Sep. 2000, 7(5):751-758.
Singh et al., "Recent Developments in Oligonucleotide Conjugation", Chemical Society Reviews, Jun. 2010, 39(6):2054-2070.
Sun et al., "In Vivo Gene Transfer of CD40 Ligand into Colon Cancer Cells Induces Local Production of Cytokines and Chemokines, Tumor Eradication and Protective Antitumor Immunity", Gene Therapy, 2000, 7(17):1467-1476.
Surman et al., "Generation of Polyclonal Rabbit Antisera to Mouse Melanoma Associated Antigens Using Gene Gun Immunization", Journal of Immunological Methods, Jun. 1998, 214(1-2):51-62.
Susonov et al., "Stereochemical Control of DNA Biosynthesis", Nucleic Acids Research, Mar. 2000, 28(5):1170-1175.
Tarhini et al., "Differing Patterns of Circulating Regulatory T-Cells and Myeloid Derived Suppressor Cells in Metastatic Melanoma Patients Receiving Anti-CTLA4 Antibody and Interferon-α or TLR-9 Agonist and GM-CSF with Peptide Vaccination", Journal of Immunotherapy, Nov. 2012, 35(9):702-710.
Tondelli et al., "Terminally L-modified Oligonucleotides: Pairing, Stability and Biological Properties", Anticancer Drugs, Feb. 1996, 7(2):189-194.
Urata et al., "NMR Study of a Heterochiral DNA: Stable Watson-Crick-Type base-pairing between the Enantiomeric Residues", Journal of the American Chemical Society, 1993, 115(21):9852-9853.
Urata et al., "Synthesis and Properties of Mirror-image DNA", Nucleic Acids Research, 1992, 20(13):3325-3332.
Vater et al., "Turning Mirror-image Oligonucleotides into Drugs: The Evolution of Spiegelmer(®) Therapeutics", Drug Discovery Today, Jan. 2015, 20(1):147-155.
Vereecque et al., "Gene Transfer of GM-CSF, CD80 and CD154 cDNA Enhances Survival in a Murine Model of Acute Leukemia with Persistence of a Minimal Residual Disease", Gene Therapy, 2000, 7(15):1312-1316.
Verthelyi et al., "Human Peripheral Blood Cells Differentially Recognize and Respond to Two Distinct CpG Motifs", The Journal of Immunology, 2001, 166(4):2372-2377.
Vibholm et al., "Short-Course Toll-Like Receptor 9 Agonist Treatment Impacts Innate Immunity and Plasma Viremia in Individuals with Human Immunodeficiency Virus Infection", Clinical Infectious Diseases, Jun. 15, 2017, 64(12):1686-1695.
Walker et al., "Immunostimulatory Oligodeoxynucleotides Promote Protective Immunity and Provide Systemic Therapy for Leishmaniasis via IL-12- and IFN-?? -Dependent Mechanisms", Proceedings of the National Academy of Sciences, Jun. 1999, 96(12):6970-6975.
Wang et al., "CpG-Independent Synergistic Induction of β-Chemokines and a Dendritic Cell Phenotype by Orthophosphorothioate Oligodeoxynucleotides and Granulocyte-Macrophage Colony-Stimulating Factor in Elutriated Human Primary Monocytes", The Journal of Immunology, May 15, 2005, 174(10):6113-6121.

(56) References Cited

OTHER PUBLICATIONS

Weber et al., "Tumor Immunity and Autoimmunity Induced by Immunization with Homologous DNA", Journal of Clinical Investigation, Sep. 1998, 102(6):1258-1264.
Weeratna et al., "Reduction of Antigen Expression from DNA Vaccines by Coadministered Oligodeoxynucleotides", Antisense and Nucleic Acid Drug Development, Aug. 1998, 8(4):351-356.
Weihrauch et al., "Phase I Clinical Study of the Toll-like Receptor 9 Agonist MGN1703 in Patients with Metastatic Solid Tumours", European Journal of Cancer, Jan. 1, 2015, 51(2):146-156.
Weiner et al., "The Immunobiology and Clinical Potential of Immunostimulatory CpG Oligodeoxynucleotides", Journal of Leukocyte Biology, Oct. 2000, 68(4):455-463.
Williams et al., "Bioactive and Nuclease-resistant L-DNA Ligand of Vasopressin", Proceedings of the National Academy of Sciences, Oct. 14, 1997, 94(21):11285-11290.
Wittig et al., "MGN1703, an Immunomodulator and Toll-like Receptor 9 (TLR-9) Agonist: From Bench to Bedside", Critical Reviews in Oncology/Hematology, Apr. 2015, 94(1):31-44.
Wittig et al., "Therapeutic Vaccination Against Metastatic Carcinoma by Expression-modulated and Immunomodified Autologous Tumor Cells: A First Clinical Phase I/II Trial", Human Gene Therapy, 2001, 12(3):267-278.
Wlotzka et al., "In Vivo Properties of an Anti-GnRH Spiegelmer: An Example of an Oligonucleotide-based Therapeutic Substance Class", Proceedings of the National Academy of Sciences, Jun. 25, 2002, 99(13):8898-8902.
Wolchok et al., "Guidelines for the Evaluation of Immune Therapy Activity in Solid Tumors: Immune-Related Response Criteria", Clinical Cancer Research, Nov. 24, 2009, 15(23):7412-7420(10 pages).
Wolters et al., "Construction of a 42 Base Pair Double Stranded DNA Microcircle", Nucleic Acids Research, Jul. 11, 1989, 17(13):5163-5172.
Wu et al., "Natural Killer T Cells and Autoimmune Disease", Current Molecular Medicine, Feb. 2009, 9(1):4-14.
Zachariae et al., "Properties Of Monocyte Chemotactic And Activating Factor (MCAF) Purified From A Human Fibrosarcoma Cell Line", The Journal of Experimental Medicine, Jun. 1990, 171(6):2177-2182.
Zdrazilova-Dubska et al., "NKT-like Cells are Expanded in Solid Tumour Patients", Klinicka Onkologie, 2012, 25(Suppl. 2):2S21-2S25.
Zhao et al., "Comparison of Cellular Binding and Uptake of Antisense Phosphodiester, Phosphorothioate, and Mixed Phosphorothioate and Methylphosphonate Oligonucleotides", Antisense Research and Development, 1993, 3(1):53-66.
Zhao et al., "Site Of Chemical Modifications in CpG Containing Phosphorothioate Oligodeoxynucleotide Modulates Its Immunostimulatory Activity", Bioorganic & Medicinal Chemistry Letters, Dec. 20, 1999, 9(24):3453-3458.
Translation of the communication issued by the Japanese Patent Office in Japanese Application No. 2016-515715, dated Nov. 29, 2017.
Translation of the communication issued by the Japanese Patent Office in Japanese Application No. 2016-515715, dated Jan. 17, 2017.
Sara Mangsbo, "Immunological Checkpoint Blockade and TLR Stimulation for Improved Cancer Therapy", Acta Universitatis Upsaliensis. Digital Comprehensive Summaries of Uppsala Dissertations from the Faculty of Medicine 506, Dec. 15, 2009, pp. 1-84, XP055275073.
Jaikumar Duraiswamy et al., "Therapeutic PD-1 Pathway Blockade Augments with Other Modalities of Immunotherapy T-Cell Function to Prevent Immune Decline in Ovarian Cancer", Cancer Research, Dec. 1, 2013, pp. 6900-6912, vol. 73, No. 23.
Julien Fourcade et al., "PD-1 and Tim-3 Regulate the Expansion of Tumor Antigen—Specific CD8+ T Cells Induced by Melanoma Vaccines", Cancer Research, Feb. 15, 2014, pp. 1045-1055, vol. 74, No. 4.
Raymond M. Wong et al., "TLR-9 signaling and TCR stimulation co-regulate CD8+ T cell-associated PD-1 expression", Immunology Letters, Dec. 2, 2009, pp. 60-67, vol. 127, No. 1.
Aurelien Marabelle et al., "Depleting tumor-specific Tregs at a single site eradicates disseminated tumors", Journal of Clinical Investigation, American Society for Clinical Investigation, Jun. 1, 2013, pp. 2447-2463, vol. 123, No. 6.
Luxembourg Search Report for LU 92821, dated May 25, 2016.
International Search Report for PCT/EP2016/071314, dated Feb. 16, 2017.
Carr et al. (Oct. 21, 2000) "Adverse Effects of Antiretroviral Therapy", The Lancet, 356(9239):1423-1430.
Scheller et al. (May 21, 2004) "CpG Oligodeoxynucleotides Activate HIV Replication in Latently Infected Human T Cells", Journal of Biological Chemistry, 279(21):21897-21902.
Osterlehner et al. (Nov. 2011) "Promoter Methylation And Transgene Copy Numbers Predict Unstable Protein Production In Recombinant Chinese Hamster Ovary Cell Lines", Biotechnology and Bioengineering, 108(11):2670-2681.
Mueller, S. (Ed.) (2008) Nucleic Acids from A to Z: A Concise Encyclopedia. Wiley-VCH: Weinheim, Germany, pp. 68, 71, 86, 5 pages.
Roitt et al. (1998), Chapter 19: Vaccination. In Immunology (5th ed.). Mosby:: London, 13 pages.
Roitt et al. (1998), Chapter 20: Tumour Immunology. In Immunology (5th ed.). Mosby:: London, 11 pages.
International Search Report and Written Opinion for International Patent Application No. PCT/DE04/01096, dated Nov. 12, 2004.
International Preliminary Examination Report for PCT International Application No. PCT/DE04/01096, dated Oct. 4, 2006.
International Search Report for PCT Patent International Application No. PCT/DE2000/00565, dated Aug. 18, 2000.
International Preliminary Examination Report for PCT International Application No. PCT/DE00/00565, completed on Oct. 23, 2001.
Guiducci, et al. (2009) Signalling Pathways Leading To IFN-alpha Production In Human Plasmacytoid Dendritic Cell And The Possible Use Of Agonists Or Antagonists Of TLR7 And TLR9 In Clinical Indications, Journal of Internal Medicine 265(1):43-57.
Klinman (2004) Immunotherapeutic Uses of CpG Oligodeoxynucleotides, Nature Reviews Immunology 4(4):249-259.
Klinman, et al. (2004) Use of CpG Oligodeoxynucleotides as Immune Adjuvants, Immunological Reviews 199(1):201-216.
Krieg (2004) Antitumor Applications of Stimulating Toll-like Receptor 9 with CpG Oligodeoxynucleotides, Current Oncology Reports 6(2):88-95.
Agrawal, et al., "Medicinal Chemistry and Therapeutic Potential of CpG DNA", Trends in Molecular Medicine, 8(3):114-121 (2002).
Hartmann, et al., "Delineation of a CpG Phosphorothioate Oligodeoxynucleotide for Activating Primate Immune Responses In Vitro and In Vivo", Journal of Immunology, 164(3):1617-1624 (2000).
Krieg, "The CpG Motif: Implications for Clinical Immunology", BioDrugs, 10(5):341-346 (1998).
Watanabe, et al. "Endogenous siRNAs from Naturally Formed dsRNAs Regulate Transcripts in Mouse Oocytes", Nature, 453:539-544 (2008).
Yamamoto, et al., "Ability of Oligonucleotides with Certain Palindromes to Induce Interferon Production and Augment Natural Killer Cell Activity Is Associated with Their Base Length", Antisense Research and Development, 4(2):119-122 (1994).
Zhao, et al., "Effect of Different Chemically Modified Oligodeoxynucleotides on Immune Stimulation", Biochemical Pharmacology, 51(2):173-182 (1996).

* cited by examiner

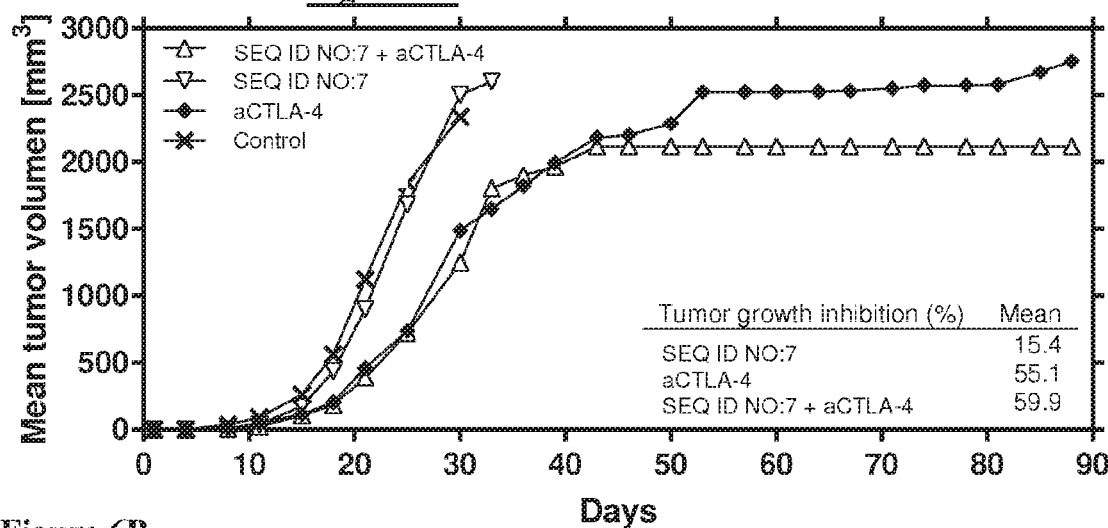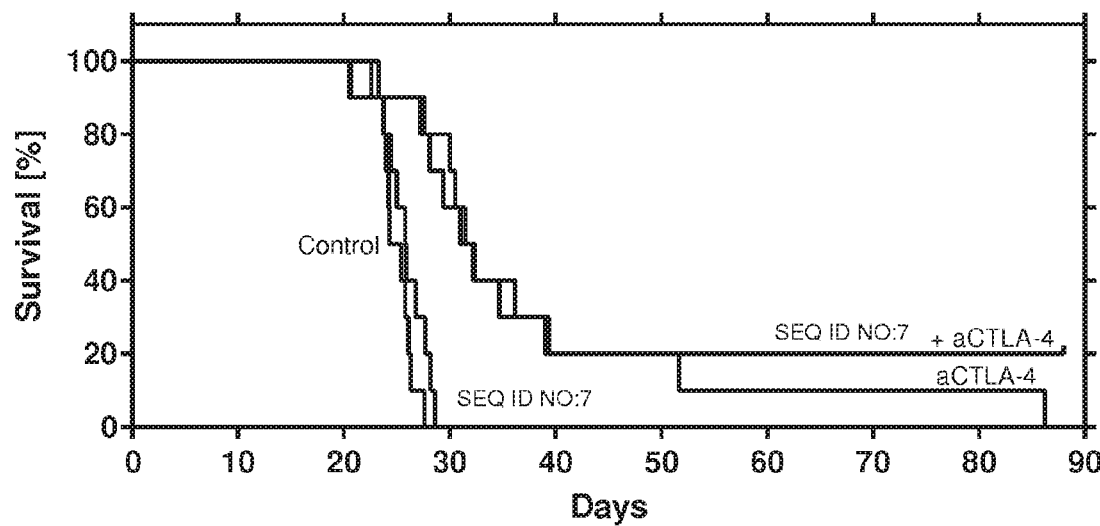

SEQUENCE LISTING

<160> NUMBER OF SEQ ID NOS: 12

<210> SEQ ID NO 1
<211> LENGTH: 48
<212> TYPE: DNA

<213> ORGANISM: Artificial Sequence
<220> FEATURE:
<223> OTHER INFORMATION: synthetic oligodeoxynucleotide

<400> SEQUENCE: 1
gttcctggag acgttcttag gaacgttctc cttgacgttg gagagaac        48

<210> SEQ ID NO 2
<211> LENGTH: 60
<212> TYPE: DNA
<213> ORGANISM: Artificial Sequence
<220> FEATURE:
<223> OTHER INFORMATION: synthetic oligodeoxynucleotide

<400> SEQUENCE: 2
accttccttg tactaacgtt gcctcaagga aggttgatct tcataacgtt gcctagatca        60

<210> SEQ ID NO 3
<211> LENGTH: 18
<212> TYPE: DNA
<213> ORGANISM: Artificial Sequence
<220> FEATURE:
<223> OTHER INFORMATION: synthetic oligodeoxynucleotide

<400> SEQUENCE: 3
aacgttcttc ggggcgtt        18

<210> SEQ ID NO 4
<211> LENGTH: 58
<212> TYPE: DNA
<213> ORGANISM: Artificial Sequence
<220> FEATURE:
<223> OTHER INFORMATION: synthetic oligodeoxynucleotide

<400> SEQUENCE: 4
aggtggtaac ccctaggggt taccaccttc atcgtcgttt tgtcgttttg tcgttctt        58

<210> SEQ ID NO 5
<211> LENGTH: 116
<212> TYPE: DNA
<213> ORGANISM: Artificial Sequence
<220> FEATURE:
<223> OTHER INFORMATION: synthetic oligodeoxynucleotide

<400> SEQUENCE: 5
cctaggggtt accaccttca ttggaaaacg ttcttcgggg cgttcttagg tggtaacccc        60
taggggttac caccttcatt ggaaaacgtt cttcggggcg ttcttaggtg gtaacc        116

<210> SEQ ID NO 6
<211> LENGTH: 58
<212> TYPE: DNA
<213> ORGANISM: Artificial Sequence
<220> FEATURE:
<223> OTHER INFORMATION: synthetic oligodeoxynuclotide

<400> SEQUENCE: 6
aggtggtaac ccctaggggt taccaccttc atcgtcgttt tgtcgttttg tcgttctt        58

<210> SEQ ID NO 7
<211> LENGTH: 33
<212> TYPE: DNA
<213> ORGANISM: Artificial Sequence
<220> FEATURE:
<223> OTHER INFORMATION: synthetic oligodeoxynucleotide; Position 31 and
      32 in L-conformation

```
<400> SEQUENCE: 7
ggggtcatta aaacgtgacg tgacgttctt ttt                              33

<210> SEQ ID NO 8
<211> LENGTH: 37
<212> TYPE: DNA
<213> ORGANISM: Artificial Sequence
<220> FEATURE:
<223> OTHER INFORMATION: synthetic oligodeoxynucleotide; Positions 1, 2
      and 35 and 36 in L-conformation

<400> SEQUENCE: 8
ggggggggtc attaaaacgt gacgtgacgt tcttttt                          37

<210> SEQ ID NO 9
<211> LENGTH: 32
<212> TYPE: DNA
<213> ORGANISM: Artificial Sequence
<220> FEATURE:
<223> OTHER INFORMATION: synthetic oligodeoxynucleotide; positions 30
      and 31 in L-conformation

<400> SEQUENCE: 9
ggggtcatta aacgtgacgt gacgttcttt tt                               32

<210> SEQ ID NO 10
<211> LENGTH: 34
<212> TYPE: DNA
<213> ORGANISM: Artificial Sequence
<220> FEATURE:
<223> OTHER INFORMATION: synthetic oligodeoxynucleotide; positions 32
      and 33 in L-conformation

<400> SEQUENCE: 10
ggggtcatta aacgttcttc ggggcgttct tttt                             34

<210> SEQ ID NO 11
<211> LENGTH: 39
<212> TYPE: DNA
<213> ORGANISM: Artificial Sequence
<220> FEATURE:
<223> OTHER INFORMATION: synthetic oligodeoxynucleotide; positions 37
      and 38 in L-conformation

<400> SEQUENCE: 11
ggggtcatta aatcgtcgtt ttgtcgtttt gtcgttttt                        39

<210> SEQ ID NO 12
<211> LENGTH: 21
<212> TYPE: DNA
<213> ORGANISM: Artificial Sequence
<220> FEATURE:
<223> OTHER INFORMATION: synthetic oligodeoxynucleotide; positions 1, 2
      and 19 and 20 in L-conformation

<400> SEQUENCE: 12
gggggacgat cgtcggggg t                                            21
```

COMBINATION COMPRISING IMMUNOSTIMULATORY OLIGONUCLEOTIDES

CROSS REFERENCE TO RELATED APPLICATIONS

This application is a continuation of U.S. application Ser. No. 16/450,324, filed on Jun. 26, 2019 (now allowed), which is a Divisional of U.S. application Ser. No. 15/756,798, filed Mar. 1, 2018, (now U.S. Pat. No. 10,487,333, issued Nov. 26, 2019), which is a National Stage of International Application No. PCT/EP2016/071314 filed Sep. 9, 2016, claiming priority based on Luxembourg Patent Application No. 92821, filed Sep. 9, 2015.

DESCRIPTION

Field of the Invention

The invention relates to a combination and its use for the treatment of diseases.

Brief Description of the Related Art

The term "immunotherapy" defines the treatment of diseases by stimulating, inducing, enhancing or suppressing an immune response. The strategy of immunotherapies is to fight diseases, such as cancer, infectious diseases, allergy and asthma.

A variety of active agents, so called immunomodulators, that can be used in immunotherapy are known. Most established immunomodulators belong to small molecules or nucleic acids, many of which interact with the toll-like receptor system. Most known immunomodifying short DNA sequences contain an unmethylated cytosine guanine motif (CG motif), which has been described by Krieg et al. (Nature 1995 374: 6522 546-549). The occurrence of unmethylated CG motifs is substantially suppressed in the genome of eukaryotes compared to prokaryotes or viruses. Therefore, DNA molecules containing such a motif have evolved as a natural "danger signal" and trigger the immune system in the fight against prokaryotic or viral pathogens. This can be exploited therapeutically or prophylactically by using such sequences to treat or prevent infectious diseases with immunotherapy. A particular emphasis has in recent years been put on the use of such immunomodulators in cancer therapy, with the aim of activating the patient's own immune system to fight against tumors.

DNA constructs comprising unmethylated CG motifs are able to elicit a considerable physiological effect by strongly stimulating effector cells of the innate immune system including dendritic cells, macrophages, natural killer (NK) and NKT cells. Unmethylated CG motifs are detected by the innate immune pattern recognition receptor Toll-like receptor (TLR) 9. While the exact recognition mechanism is not yet fully understood, significant progress in unraveling the underlying pathways has been made (A. Krieg, Nat. Rev. Drug Disc., 5:471-484, 2006).

It is assumed that upon binding of DNA constructs containing unmethylated CGs to the receptor, multiple signal cascades are activated in responding cells. By upregulation of characteristic surface molecules and secretion of cytokines, adaptive immunity with a predominant Th1 pattern is induced. Such constructs can be used in combination with, for example, antibodies, chemotherapy or radiation therapy, vaccines or cytokines. Allergic diseases and asthma are mostly Th2-mediated. By increasing the ratio of Th1/Th2, the Th2-mediated responses are attenuated and thereby these types of diseases can be treated or prevented.

Surface molecules, which are unregulated by the TLR-9 pathway, include, for example, CD40, CD69, CD80, CD86 or CD169, depending on the cell type. The enhanced secretion of cytokines is also characteristic for distinct cell types; cytokines include, for example, macrophage inflammatory proteins (MIP)-1alpha, MIP-1beta, interleukin (IL)-6, IL-8, interferon (IFN)-alpha, tumor necrosis factor (TNF)-alpha, IFN-gamma, monocyte chemotactic protein (MCP)-1 or IFN-gamma-induced protein of 10 kDa (IP-10).

In order to prevent or treat diseases, vaccination has been proven as a very effective approach. To ensure a strong and durable immune response, adjuvants capable of stimulating antigen-presenting cells such as dendritic cells, are usually administered together with the antigen, and for that purpose TLR9 agonists have been shown to be potent immunostimulants.

Preclinical and ongoing clinical studies support the use of TLR-9 agonists as immunomodulators and/or adjuvants, and prove their anti-tumor effect by enhancing both the humoral and cellular responses.

Independently of any explanations of the underlying mechanisms by which unmethylated CG motifs influence or modulate an immune response, many approaches were developed for modulation of the immune system by using such motifs. The WO 1998/018810 discloses that immunostimulatory sequences containing unmethylated CG motifs are even more effective when they are part of a single strand. However, administering an open-chained single-stranded DNA molecule is not practicable due to the quick degradation of single-stranded nucleic acids. Consequently, different methods for the protection of single- or double-stranded DNA constructs comprising an unmethylated CG motif were developed.

To achieve resistance against the degradation by DNA nucleases the phosphodiester bonds in the backbone of a nucleic acid polymer are frequently modified to phosphorothioates. Besides a somewhat less stimulatory activity of such phosphorothioate-protected nucleic acids clinical trials within the last years showed that the toxicity of a phosphorothioate-protection exclude or severely limit such nucleic acids from any use in pharmaceutical compositions or medicaments.

From the four classes of known activators with distinct immunomodulation profiles all members except two comprise linear DNA molecules. One exception is disclosed in EP 1 196 178. This document discloses short deoxyribonucleic acid molecules, comprising a partially single-stranded, dumbbell-shaped, covalently closed sequence of nucleotide residues comprising CG motifs ("dSLIM") consisting entirely of natural DNA. According to the disclosure of the EP 1 196 178 the CG motifs are located within the single-stranded loops at both ends of the double-stranded stem of the disclosed molecule or within the double-stranded stem. The single-stranded hairpin loops protect a double-stranded stem from degradation by DNA nucleases within or outside of the cell. GB 1402847.6 discloses a somewhat similar dumbbell structure utilizing a different sequence.

Another exception from linear oligonucleotides is disclosed in WO 2012/085291. This document teaches DNA constructs comprising nucleotides in L-conformation. According to the data disclosed in WO 2012/085291, the number of nucleotides in L-conformation and their position within the DNA construct influences the immunostimulatory capability of the DNA construct. A DNA construct comprising only nucleotides in L-conformation does for instance not efficiently stimulate the immune system.

Document WO 2010/039137 discloses immune regulatory oligonucleotides as antagonists for TLR mediated diseases having one or more chemical modifications in the sequence flanking an immune stimulatory motif and/or in an oligonucleotide motif that would be immune stimulatory but for the modification. Thus, the intention of the disclosed oligonucleotides of WO 2010/039137 is to suppress an immune response caused by TLRs.

WO 2005/042018 describes new so-called C-class CpG oligonucleotides, wherein a c-class oligonucleotide is characterised by CpG sequences, generally positioned at or near the 5' end or 3' end of the molecule, and a GC-rich palindrome motif, generally positioned at or near the other end of the molecule. The document discloses variations of the palindromic sequence of a c-class DNA.

Document WO 2015/124614 discloses covalently closed DNA construct, a pharmaceutical composition and a vaccine and their use for the modulation of the immune system, wherein the DNA construct comprises specific DNA sequences.

The strong stimulation of a cellular immune response makes it possible to influence regulatory circuits, and without such intervention no satisfactory immune activity would occur in the patient. This includes inducing a response to "weak" antigens, i.e. non-activating within MHC-I presentation, for example breakpoint peptides from chromosomal translocations or mutated oncogenes, often occurring in tumour diseases (Melief C J, Kast W M; T-cell immunotherapy of cancer; Res Immunol 1991 June-August; 142(5-6):425-9; also: Pasternak G, Hochhaus A, Schultheis B, Hehlmann R; Chronic myelogenous leukemia: molecular and cellular aspects; J Cancer Res Clin Oncol 1998; 124 (12):643-60). It may also be desirable to break the tolerance to autoantigens such as the tyrosinase or tyrosinhydroxylase expressed in tumour cells of malignant melanoma and represented in MHC-I. (Weber L W, Bowne W B, Wolchok J D, Srinivasan R, Qin J, Moroi Y, Clynes R, Song P, Lewis J J, Houghton A N; Tumor immunity and autoimmunity induced by immunization with homologous DNA; J Clin Invest 1998 Sep. 15; 102(6):1258-64; Surman D R, Irvine K R, Shulman E P, Allweis T M, Rosenberg S A, Restifo N J; Generation of polyclonal rabbit antisera to mouse melanoma associated antigens using gene gun immunization; Immunol Methods; 1998 May 1; 214(1-2):51-62).

Another, extremely important aspect is the adjuvant effect of ISS in prophylactic vaccinations as well as the possibility of re-polarizing the reaction of an existing infection from a type-2 response to a type-1 response, thus enabling the pathogen to be controlled (Kovarik J, et al. CpG oligodeoxynucleotides can circumvent the Th2 polarization of neonatal responses to vaccines but may fail to fully redirect Th2 responses established by neonatal priming; J Immunol. 1999 Feb. 1; 162(3):1611-7). It has been demonstrated for a large number of pathogens that the type of immune response has a decisive influence on the course of the infection or on the patient's ability to survive. As far as allergic reactions represent a type-2 overshoot response, ISS is expected to provide a therapeutic effect for indications of this kind as well.

It has been observed that certain sequences containing CpGs possess a characteristic which neutralises ISS-induced stimulation, i.e. that sequences of this kind are able to suppress the stimulatory effect of ISS when added to them (Krieg A M, Wu T, Weeratna R, Efler S M, Love-Homan L, Yang L, Yi A K, Short D, Davis H L; Sequence motifs in adenoviral DNA block immune activation by stimulatory CpG motifs; Proc Natl Acad Sci USA 1998 Oct. 13; 95(21): 12631-6). Without having fully explained the underlying mechanism of the effect of these sequence motifs described as neutralising CpG motifs ("CpG-N"), the authors of the publication quoted here imply that this effect is limited to blocking stimulation by ISS. As long as the mechanism of immune induction by ISS is not explained, one cannot rule out the possibility that these CpG-N motifs also possess other immunomodifying properties of therapeutical significance.

There is at least one human disease, systemic lupus erythematosus, which is characterized by the confirmed existence of anti-DNA antibodies in patient serum, and where it is suspected that a reaction to bacterial ISS has aetiological reasons (Krieg A M, CpG DNA: a pathogenic factor in systemic lupus erythematosus?, J Clin Immunol 1995 November; 15(6):284-92). In these cases and in other indications, blocking the underlying mechanisms using CpG-N motifs would be beneficial.

Independent of any explanation of the underlying mechanisms, the potential of CpG sequences for influencing the immune response is considerable and has generated sudden and widespread scientific interest in the phenomenon as well as in exploring the possibilities for therapeutic and prophylactic applications where infections, tumours and immune deficiencies are concerned.

The literature concerning ISS states (see e.g. WO09818810A1, p. 17, ll 29-30), and this is confirmed by the invention described (see below), that immunostimulatory sequences containing CpGs are more effective when they occur as single strands. Administering short, open-chain, single-strand ISS oligodeoxynucleotides with the objective of immune modification is the next logical step to take, and is the subject of numerous experimental approaches for treating infectious illnesses, tumours and autoimmune diseases. However, open-chain, single-strand oligodeoxynucleotides are degraded very quickly by extracellular and intracellular exonucleases and are therefore very difficult to use in in-vivo applications. The nucleases mentioned display considerably reduced enzymatic activity when compared to modified phospho-ester bonds in the backbone of nucleic acid polymers; this has led to phosphor thioesters ("thioates") or reduced phosphor bonds (phosphonates) in chiral or achiral form being used in applications where single-strand nucleic acid molecules are to be administered to the patient. These modified compounds can be produced by solid phase synthesis, yet to some extent only by considerably more complicated methods by comparison with classic DNA amidite synthesis. These compounds are known from antisense research; in clinical studies of antisense strategies, however, it was also demonstrated that they have considerable side effects, particularly on the blood coagulation system and complement system (see e.g. Sheehan and Lan, Blood 92, 1617-1625 (1998)). In connection with the use of thiophosphoric acid derivatives for nuclease protection of ISS it was also demonstrated that the sequences display less stimulatory activity when those cytosine-guanosine residues which are actually effective are themselves protected by the flanking sequences required for the activity itself (see WO 98/18810).

The teaching concerning use and production of immunostimulatory ISS containing CpGs is comprehensively described in WO 98/18810, as well as in the documents quoted therein. The necessity for protecting oligodeoxynucleotides from exonucleases is described in detail in WO 98/18810. A number of solutions are presented for solving the problem of insufficient in vivo stability, which are however expressly limited to single-strand linear ODNs; mention is made of thiophosphate esters, dithiophosphate esters or phosphonates. The possibility of stabilising the ODN by creating secondary structures, in particular a stem-loop, is noted in WO 98/18810. Production and use of phosphorothioate oligomers in connection with immunostimulatory sequences is described in U.S. Pat. Nos. 5,663,153, 5,723,335 as well as in U.S. Pat. No. 5,856,462.

A different strategy for protecting single-strand sequences is described in U.S. Pat. No. 5,750,669. Here the ends of the oligomers are linked with nucleoside residues connected by 5'-5' and 3'-3' bonds, which block exonucleolytic degradation.

Double stem-loop or covalently closed, dumbbell-shaped ODNs are known from experimental approaches in which competition in bonding sites for DNA-binding proteins, as well as transcription factors were the focus of research (Lim et al. 1997, Nuc. Acids Res. 25, 575-581; Blumenfeld et al., Nuc. Acids Res. 1993, 21, 3405-3411).

The T cell response of the human immune system is regulated by multiple T-cell regulating molecules to avoid over-activation of the immune system on healthy cells (Pardoll D M. Nat Rev Cancer. 2012; 12(4):252-264; Sharma P, Wagner K, Wolchok J D, Allison J P. Nat Rev Cancer. 2011; 11(11):805-812). Such T-cell regulating molecules are summarized as "T-cell regulator" within the context of the instant disclosure and comprise checkpoint inhibitors and co-stimulants. Tumor cells often take advantage of these regulatory systems to escape detection by the immune system. Inhibition of a checkpoint of the immune system and co-stimulation of the T-cell system may enhance the anti-tumor immune response. The blockade of immune checkpoints and thus liberation of tumor-specific T cells to exert their effector function against tumor cells has demonstrated efficacy in cancer settings, and clinical trials are ongoing (Hodi F S, O'Day S J, McDermott D F, et al. N Engl J Med. 2010; 363(8):711-723; Robert C, Thomas L, Bondarenko I, et al. N Engl J Med. 2011; 364(26):2517-2526; Wolchok J D, H. Kluger, M. K. Callahan, et al. N Engl J Med, 369 (2013), pp. 122-133).

Cytotoxic T-lymphocyte antigen (CTLA)-4 and programmed cell death (PD)-1 represent two checkpoints, which have been studied most extensively as targets for cancer therapy so far. CTLA-4 is a potent co-inhibitor that has been shown to be aberrantly upregulated on the surface of T cells in certain cancers. It decreases T-cell activation in response to tumor cells and is thus involved in early T-lymphocyte tolerance. PD-1 has been found to be upregulated in certain tumors, inhibiting T-cell function helping the tumor to evade the immune system by playing a role in maintaining peripheral T-lymphocyte tolerance (Keir M E, Butte M J, Freeman G J, Sharpe A H, et al. Annu Rev Immunol. 2008; 26:677-704; Mahoney K M, Freeman G J, McDermott D F. Clinical Therapeutics 37(4): 764-782, 2015).

The first immune-checkpoint inhibitor approved by the US Food and Drug Administration (FDA) in 2011 was ipilimumab, a monoclonal antibody that blocks CTLA-4 for the treatment of metastatic melanoma. Blocking the interaction between PD-1 and one of its ligands, PD-L1 (also known at B7-H1 and CD274), has been reported to generate antitumor responses (Pardoll D M. Nat Rev Cancer. 2012; 12(4):252-264).

Another inhibitory molecule, lymphocyte activation gene-3 (LAG-3), a CD4 homolog that binds to MHC class II molecules, is expressed on activated T cells, B cells, NK cells, and tumor-infiltrating lymphocytes, and is thought to negatively regulate T-cell expansion by limiting T-cell activation (Pardoll D M. Nat Rev Cancer. 2012; 12(4):252-264; Goldberg M V, Drake C G. Curr Top Microbiol Immunol 2011; 344:269-78). Its blockade augments T cell proliferation and enhances anti-tumor T cell responses (Nguyen L T, Nat Rev Immunol, 2015).

Further, T-cell immunoglobulin mucin-3 (TIM-3), the ligand of which is galectin 9 (upregulated in various types of cancer), is expressed by IFN-secreting helper T (TH 1) cells, as well as dendritic cells, monocytes, and T cells [Ngiow S F, Teng M W, Smyth M J. Cancer Res. 2011; 71(246567-71]. It inhibits T helper 1 cell responses, and TIM-3 antibodies enhance antitumor immunity (Anderson A C. Curr Opin Immunol 2012; 24:213-6). When bound to its ligand, galectin-9, TIM-3 induces TH1 cell death (Zhu C, Anderson A C, Schubart A, et al. Nat Immunol. 2005; 6(12):1245-52). Studies of TIM-3-deficient mice suggest that the TIM-3 pathway inhibits the expansion and effector functions of TH 1 cells and may be important for tolerance induction of TH1 cells (Sabatos C A, Chakravarti S, Cha E, et al. Nat Immunol. 2003; 4(11):1102-10). TIM-3 has also been reported to be co-expressed with PD-1 on tumor-specific CD8+ T cells, and dual blockade of both molecules significantly enhances the in vitro proliferation and cytokine production of human T cells. In animal models, coordinate blockade of PD-1 and TIM-3 was reported to enhance anti-tumor immune responses and tumor rejection (Pardoll D M. Nat Rev Cancer. 2012; 12(4):252-264).

B- and T-lymphocyte attenuator (BTLA/CD272) was identified as an inhibitory receptor on T cells and HVEM/TNFRSF14—which is expressed on tumor cells as well as on tumor-associated endothelial cells—was shown to be the BTLA ligand. BTLA expression levels are high on tumor infiltrating lymphocytes (TIL) from patients with melanoma and BTLA-expressing T cells are inhibited in the presence of its ligand, HVEM. BTLA can inhibit the function of tumor-specific human $CD8^+$ T cells (Paulos C M, June C H. J Clin Invest 2010; 120:76-80). Thus, BTLA may also be a relevant inhibitory receptor for T cells in the tumour microenvironment and a target for checkpoint inhibition strategies (Pardoll D M. Nat Rev Cancer. 2012; 12(4):252-264).

OX40 (CD134/TNFRSF4) is a member of the TNFR super-family and is expressed by CD4 and CD8 T cells during antigen-specific priming. Ligation of OX40 on CD8 and CD4 T cells promotes their survival and expansion. Furthermore activating OX40 boosts the generation of tumor-reactive effector T cells and inhibits T-cell function. Preclinical studies demonstrated that treatment of tumor-bearing hosts with OX40 agonists resulted in tumor regression in several preclinical models (Linch S N, McNamara M J, Redmond W L. Front Oncol. 2015 5:34).

The co-stimulatory receptor CD137 (4-1BB/TNFSF9) possesses an unequaled capacity for both activation and pro-inflammatory polarization of anti-tumor lymphocytes. Co-stimulation through the CD137/4-1BB receptor activates multiple signaling cascades within the T cell, powerfully augmenting T cell activation. Stimulation of CD137 on antigen-primed T-lymphocytes increase tumor immunity and CD137 monotherapy is capable of mediating significant tumor regressions and even cures of numerous types of established murine tumors (Bartkowiak T, Curran M A. Front Oncol. 2015 5:117).

Based on this state of the art, the objective of the instant disclosure is to provide an efficient combination comprising immunostimulatory DNA constructs and its use as a medicament.

SUMMARY OF THE INVENTION

With regard to the prior art it is an objective of the instant disclosure to provide a combination of molecule binding to a T-cell regulator and an immunomodulating DNA construct in form of a non-coding sequence of deoxyribonucleotides.

The present disclosure teaches a combination comprising the components of a chemical or molecule binding to at least one of the molecules selected from the group comprising PD1, PD-L1, OX40, TIM-3, LAG3, CD137(4-1BB) for affecting their function as checkpoint inhibitors or co-stimulants; and a non-coding sequence of deoxyribonucleic acids comprising at least one sequence motif $N^1N^2CGN^3N^4$, wherein N is a nucleotide comprising A, C, T, or G, and C is deoxycytidine, G is deoxyguanosine, A is deoxyadenosine and T is deoxythymidine.

The molecule binding to a T-cell regulator may be a protein or peptide, like an antibody, which is synthetically or biologically manufactured.

The combination of the instant disclosure may comprise for $N^1N^2$ an element taken from the group of GT, GG, GA, AT and AA, and for $N^3N^4$ an element taken from the group of CT, TG and TT.

The non-coding sequence of deoxyribonucleic acids may either be linear open-chained on both sides, linear open-chained on one side of a double stranded part with a single stranded hairpin on the respective other side of the double strand or a dumbbell-shaped partially single-stranded covalently closed chain of deoxyribonucleic acids.

The combination may further comprise at least three of said sequence motifs $N^1N^2CGN^3N^4$.

It is intended for a linear open-chained non-coding sequence of deoxyribonucleic acids that it may comprise at least one nucleotide in L-conformation, wherein one of the five terminal nucleotides located at the 5'- and/or the 3'-end of a DNA single strand of the linear open-chained non-coding sequence of deoxyribonucleic acids may be in L-conformation.

The combination of the instant disclosure may further comprise at least one of the following non-coding sequences of deoxyribonucleotides

```
                                           (SEQ ID NO: 1)
a. GTTCCTGGAG ACGTTCTTAG GAACGTTCTC CTTGACGTTG

GAGAGAAC;
or
                                           (SEQ ID NO: 2)
b. ACCTTCCTTG TACTAACGTT GCCTCAAGGA AGGTTGATCT

TCATAACGTT GCCTAGATCA,
or
                                           (SEQ ID NO: 3)
c. AACGTTCTTCGGGG CGTT,
or
                                           (SEQ ID NO: 4)
d. AGGTGGTAAC CCCTAGGGGT TACCACCTTC ATCGTCGTTT

TGTCGTTTTG TCGTTCTT.
```

The combination may further comprise a non-coding sequence of deoxyribonucleic acids with a length of 40 to 200 nucleotides or of 48 to 116 nucleotides.

It is further intended that the sequence AACGTTCTTCGGGG CGTT (SEQ ID NO:3) may be part of the sequence CCTAGGGGTT ACCACCTTCA TTG-GAAAACG TTCTTCGGGG CGTTCTTAGG TGGTAACC CCTAGGGGTT ACCACCTTCA TTG-GAAAACG TTCTTCGGGG CGTTCTTAGG TGGTAACC (SEQ ID NO:5).

The sequence motif $N^1N^2CGN^3N^4$ can be part of a single stranded region of a non-coding sequence of deoxyribonucleotides, which is part of a combination according to the instant disclosure.

The combination may provide the components of both groups in a solid, liquid or gaseous form to be applied with maximal 15 mg/kg weight. This means that the dosage can be adapted to the weight of the organism to which the combination should be applied.

A method comprising the step of providing the components of a combination of the instant disclosure simultaneously, alternating or successively is another object of the invention. The non-coding sequence of deoxyribonucleic acids may be provided prior to the chemical or molecule for affecting the T-cell regulator or vice versa.

A further object of the instant disclosure is the use of the disclosed combination as a medicament or for the treatment of diseases like cancer, autoimmune diseases and inflammation.

The compounds of the disclosed combination may be administered simultaneously, alternating or successively for the treatment of cancer, autoimmune diseases and inflammation.

A use of the disclosed combination for the manufacture of a pharmaceutical or pharmaceutically preparation, including vaccines, comprising acceptable pharmaceutical salts is a further object of the instant invention. The pharmaceutical may release the compounds of the disclosed combination simultaneously, alternating or successively.

Finally, the use of a combination of the instant disclosure as an adjuvant in therapeutic or prophylactic vaccination is an object of the instant disclosure.

BRIEF DESCRIPTION OF THE FIGURES

The invention will be described on the basis of figures. It will be understood that the embodiments and aspects of the invention described in the figures are only examples and do not limit the protective scope of the claims in any way. The invention is defined by the claims and their equivalents. It will be understood by the skilled artisan that features of one aspect or embodiment of the invention can be combined with a feature of a different aspect or aspects of other embodiments of the invention. It shows:

FIG. 6A, B Anti-tumor activity of the combination of SEQ ID NO:7 with anti-CTLA-4.

DETAILED DESCRIPTION OF THE INVENTION

Figure 1A:
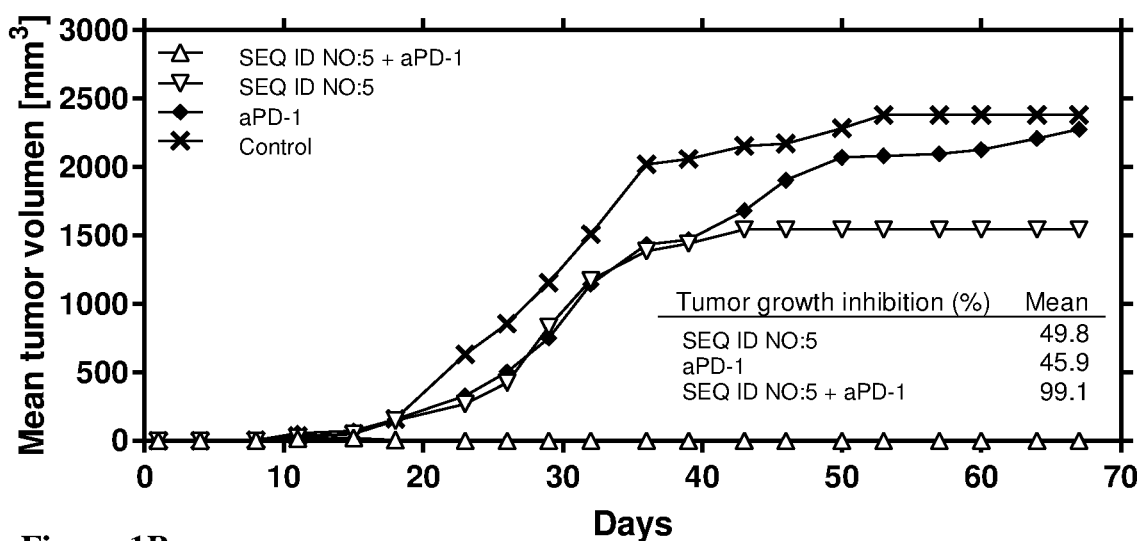
FIG. 1A, B Anti-tumor activity of the combination of SEQ ID NO:5 with anti-PD-1.

The instant invention provides a combination of a molecule binding to a so called T-cell regulator and a non coding sequence of deoxyribonucleic acids.

Within the meaning of the present disclosure a linear open-chained DNA sequence is designated as oligonucleotide, abbreviated with ODN. Said DNA sequence can be single-stranded or partially or completely double-stranded. The terms oligo, oligonucleotide and oligodeoxynucleotide are used synonymously and do not indicate a limitation of the length of the corresponding DNA sequence. The single components of oligonucleotides are nucleotides.

An oligo can be manufactured synthetically or be partially or completely of biological origin, wherein a biological origin includes genetically based methods of manufacture of DNA sequences.

L-DNA or nucleotides in L-conformation refer to nucleotides, which comprises L-deoxyribose as the sugar residue instead of the naturally occurring D-deoxyribose. L-deoxyribose is the enantiomer (mirror-image) of D-deoxyribose. Oligonucleotides partially or completely consisting of nucleotides in L-conformation can be partially or completely single- or double-stranded; however, nucleotides in L-conformation cannot hybridize to nucleotides in D-conformation (Hauser et al., Nucleic Acid Res. 2006 34: 5101-11). L-DNA is equally soluble and selective as D-DNA. Yet, L-DNA is resistant towards enzymatic exoactivity of naturally occurring enzymes, especially exonucleases, so L-DNA is protected against intracellular degradation (Urata et al., Nucleic Acids Res. 1992 20: 3325-32). Therefore, L-DNA is very widely applicable.

A "stem" according to the present disclosure shall be understood as a DNA double strand formed by base pairing either within the same oligonucleotide (which is then partially self-complementary) or within different oligonucleotides (which are partially or completely complementary). Intramolecular base-pairing designates base-pairing within the same oligonucleotide and base-pairing between different oligonucleotides is termed as intermolecular base-pairing.

A "loop" within the meaning of the present disclosure shall be understood as an unpaired, single-stranded region either within or at the end of a stem structure. A "hairpin" is a distinct combination of a stem and a loop, which occurs when two self-complementary regions of the same oligonucleotide hybridize to form a stem with an unpaired loop at one end.

A "solid phase" to which the nucleotides are covalently or non-covalently attached refers to, but is not restricted to, a column, a matrix, beads, glass including modified or functionalized glass, silica or silica-based materials including silicon and modified silicon, plastics (comprising polypropylene, polyethylene, polystyrene and copolymers of styrene and other materials, acrylics, polybutylene, polyurethanes etc.), nylon or nitrocellulose, resins, polysaccharides, carbon as well as inorganic glasses and plastics. Thus, microtiter plates are also within the scope of a solid phase according to the present disclosure.

Immunomodulation according to the present disclosure refers to immunostimulation and immunosuppression. Immunostimulation means preferentially that effector cells of the immune system are stimulated in order to proliferate, migrate, differentiate or become active in any other form. B cell proliferation for instance can be induced without co-stimulatory signals by immunostimulatory oligonucleotides, which normally require a co-stimulatory signal from helper thymocytes.

Immunosuppression on the other hand shall be understood as reducing the activation or efficacy of the immune system. Immunosuppression is generally deliberately induced to prevent for instance the rejection of a transplanted organ, to treat graft-versus-host disease after a bone marrow transplant, or for the treatment of autoimmune diseases such as, for example, rheumatoid arthritis or Crohn's disease.

In this context, immunomodulation may also refer to the influence of the nature or the character of an immune reaction, either by affecting or modifying an immune reaction, which is still developing or maturing or by modulating the character of an established immune reaction. Thus, affecting means in the context of checkpoint inhibitors to suppress their inhibitory effect, and in the context of co-stimulatory molecules to activate them.

The term "cancer" comprises cancerous diseases or a tumor being treated or prevented that is selected from the group comprising mammary carcinomas, melanoma, skin neoplasms, gastrointestinal tumors, including colon carcinomas, stomach carcinomas, pancreas carcinomas, colon cancer, small intestine cancer, ovarial carcinomas, cervical carcinomas, lung cancer, prostate cancer, kidney cell carcinomas and/or liver metastases.

Autoimmune diseases according to the present disclosure comprise rheumatoid arthritis, Crohn's disease, systemic lupus (SLE), autoimmune thyroiditis, Hashimoto's thyroiditis, multiple sclerosis, Graves' disease, myasthenia gravis, celiac disease and Addison's disease.

An agonist within the meaning of the instant disclosure and in accordance with its common definition represents a chemical or molecule that binds to another molecule, like a receptor or ligand and thus activates the molecule. In contrast to an agonist that activates, an antagonist shall be understood as a chemical or molecule that blocks the interaction of the molecule to which the antagonist binds with a respective agonist. Depending on the context, an antagonist in the understanding of the instant invention may also result in the activation of a process, because the antagonist blocks the interaction of another antagonist with a receptor for instance.

The term "pharmaceutically applicable or acceptable salts" as used herein includes salts of a compound of the combination, which are prepared with relatively nontoxic (i.e. pharmaceutically acceptable) acids or bases, depending on the particular substituents found on the compounds of the present invention. If, for example, compounds of the present invention contain acidic functionalities, base addition salts may be obtained by contacting the neutral form of such compounds with a sufficient amount of the desired base, either neat or in a suitable inert solvent. Non-limiting examples of pharmaceutically acceptable base addition salts include sodium, potassium, calcium, ammonium, organic amino, or magnesium salt, or a similar salt. If compounds of the present invention contain basic functionalities, acid addition salts may be obtained by contacting the neutral form of such compounds with a sufficient amount of the desired acid, either neat or in a suitable inert solvent. Non-limiting examples of pharmaceutically acceptable acid addition salts include those derived from inorganic acids like hydrochloric, hydrobromic, nitric, carbonic, phosphoric, partially neutralized phosphoric acids, sulfuric, partially neutralized sulfuric, hydroiodic, or phosphorous acids and the like, as well as the salts derived from relatively nontoxic organic acids like acetic, propionic, isobutyric, maleic. malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunornic acids and the like. Certain specific compounds of the present invention may contain both basic and acidic functionalities that allow the compounds to be converted into either base or acid addition salts. Contacting the salt with a base may regenerate the neutral forms of the compounds of the present invention or acid and isolating the parent compound in the conventional manner. The parent form of the compound differs from the various salt forms in certain physical properties, such as solubility in polar solvents, but otherwise the salts are equivalent to the parent form of the compound for the purposes of the present invention. The compounds of the present invention may possess chiral or asymmetric carbon atoms (optical centers) and/or double bonds. The racemates, diastereomers, geometric isomers and individual optical isomers are encompassed by the present invention. The compounds of the present invention may exist in unsolvated forms as well as solvated forms, including hydrated forms. In general, the solvated forms are equivalent to unsolvated forms and are also encompassed by the present invention. The compounds of the present invention may furthermore exist in multiple crystalline or amorphous forms.

Deoxyribonucleic acid molecules, consisting of a partially single-stranded, dumbbell-shaped, covalently closed chain of deoxyribonucleoside residues, which contain one or more sequences of the base sequence $N^1N^2C\ GN^3N^4$, wherein $N^1N^2$ is an element from the GT, GG, GA, AT or AA group, $N^3N^4$ is an element from the CT or TT group, as well as C deoxycytosine, G deoxyguanosine, A deoxyadenosine and T deoxythymidine, are used in combination with chemicals or molecules able to bind T-cell regulator of the immune system for immunostimulation in humans or higher animals.

The deoxyribonucleic acid molecules relating to the instant disclosure may have a length of up to 200 nucleotides. In particular, sequences with a length between 48 and 116 nucleotide are intended.

The dumbbell-shaped non-coding sequences of deoxyribonucleic acid molecules may comprise the base sequence $N^1N^2CGN^3N^4$ is their single-stranded regions.

The immunostimulation may take place in vitro or in vivo.

The instant disclosure provides also linear open-chained DNA sequence comprising at least one CpG motif and at least one nucleotide in L-conformation. Due to the partial/ complete L-conformation, the DNA sequence has no 5'- or 3'-ends that are accessible to exonucleases. In case that the construct has on one end of a double strand a single stranded-loop, the end is also protected against degradation. Thereby, the ODNs are in total protected against cellular degradation without having the need to use a phosphorothioate backbone, which has been shown to be toxic. In addition, the ODNs only consist of a minimum number of nucleotides, which makes them small and thereby easy to transfect into cells.

The non-coding sequence of ddeoxyribonucleic acids comprising at least one sequence motif $N^1N^2CGN^3N^4$ can be single-stranded or partially or completely double-stranded. This includes base-pairing within the same molecule (intramolecular) or within different molecules (intermolecular) or any combination thereof. It is also possible that the construct comprises at least one unpaired, single-stranded region. As a further embodiment, hairpin structures are included. Due to the partial or complete L-conformation, a longer half-life of the construct is ensured as nucleotides in L-conformation are not subject to degradation.

It is also within the scope of the instant disclosure that at least two molecules, which are single-stranded or partially or completely double-stranded can ligate to each other to form multimeric constructs. These multimeric constructs thus incorporate at least as many CpG motifs as ligation partners, tightly packed within one molecule, and are therefore expected to elicit also a considerable immune response as part of the combination with T-cell regulators. The resulting single-stranded or partially or completely double-stranded multimeric constructs can either be covalently closed comprising nucleotides in L-conformation within the molecule or open multimeric constructs comprising nucleotides in L-conformation at the 5'- and/or the 3'-end for protection against cellular degradation.

The disclosure further comprises chemical modifications of at least one nucleotide in the non-coding sequence of deoxyribonucleic acids comprising at least one sequence motif $N^1N^2CGN^3N^4$ with a functional group selected from the group comprising carboxyl, amine, amide, aldimine, ketal, acetal, ester, ether, disulfide, thiol and aldehyde groups. This allows coupling of the DNA construct to a compound selected from the group comprising peptides, proteins, carbohydrates, antibodies, synthetic molecules, polymers, micro projectiles, metal particles or a solid phase by, for example, adsorption, covalent or ionic bonding.

The modification can be specifically selected for the respective purpose. The construct can thus be used, for example, to shuttle other molecules to the specific cell responding to the CpG motif/s incorporated. In addition, it is possible by such modifications to couple the construct to micro projectiles, which can be used to transfer the construct into the cell. The construct can also be coupled to a solid phase, e. g. a microtiter plate.

Experiments described below were performed to investigate the influence of combining non-coding sequences of deoxyribonucleic acids with T-cell regulators. The experiments were conducted using dumbbell-shaped comprising the sequence motif $N^1N^2CGN^3N^4$, linear open-chained non-coding sequence of deoxyribonucleic acids comprising $N^1N^2CGN^3N^4$, wherein those constructs comprise nucleotides in L-conformation to prevent them from degradation. In addition, the effect of combining T-cell regulators with a non-coding sequence of deoxyribonucleic acids comprising $N^1N^2CGN^3N^4$ and twice the sequence of SEQ ID NO:4 were be investigated. T-cell regulators antibodies binding to PD1, PD-L1, OX40, LAG-3, TIM3 and CD137(4-1BB) were used in a mouse model with injected human tumors. The effect on therapy after a growth phase is described in more detail below on growth of tumors in comparison to control groups.

The experiments compare dosage regimen with simultaneous, alternating or successive application of the components of the combination of the instant disclosure. In addition to the qualitative application of the compounds it was investigated whether reduced amounts of T-cell regulator are necessary for achieving comparable or even better results in applying the checkpoint inhibitor without a non-coding DNA sequence comprising a $N^1N^2CGN^3N^4$ sequence motif.

The in vitro analysis of the combinatory potential of TLR9 agonists with molecules binding to T-cell regulators comprises the use of in vitro cell culture system of human PBMC for evaluation of their T cells responses after stimulation. Stimulation of PBMC will be achieved with a mixture of immunogenic peptides from CMV, EBV, influenza and tetanus-toxin in the presence of antibodies against immunological T-cell regulators (e.g. PD-1, PD-L1, etc.) and TLR9 agonists (i.e. SEQ ID NO:5, SEQ ID NO:7, SEQ ID NO:10, SEQ ID NO:6).

The quantification of cytokines (IL-2 and IFN-gamma) in cell culture supernatants was determined. Although this in vitro cell culture system cannot mirror the complex interactions of immune cells in vivo, it provides evidences for an advantage of the combination of those TLR9 agonists.

DETAILED DESCRIPTION OF THE FIGURES

The combination of SEQ ID NO:5 with anti-PD-1 showed a surprisingly vastly increased anti-tumor effect compared to either anti-PD-1 or SEQ ID NO:5 monotherapy in a mouse A20 tumor model.

Figure 1B:
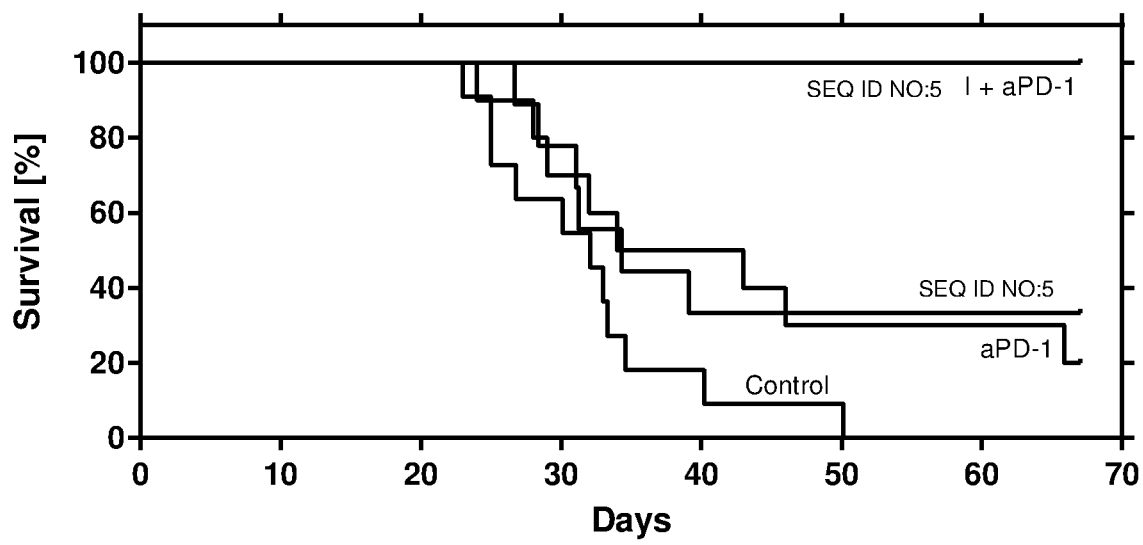

Tumor growth was surprisingly nearly completely inhibited by the combination of SEQ ID NO:5 and PD-1 (FIG. 1A, B). 9-12 mice per group were inoculated s.c. with A20 murine tumor cells and injected with SEQ ID NO:5 (250 µg/application, i.tu. on day 14, 16, 19, 21, 23, 26, 28, 30, 33 and 35), anti-PD-1 (100 µg/application i.p. on day 8, 11, 16 and 19), or both. Injection of vehicle (i.tu.) served as control. FIG. 1A shows the mean tumor growth—inlay, mean tumor growth inhibition from day 18 to 32 (at day 29: 46.0% for SEQ ID NO:5, 54.2% for anti-PD-1, 99.9% for the combination). FIG. 1B shows a Kaplan-Meier survival plot.

Figure 2:
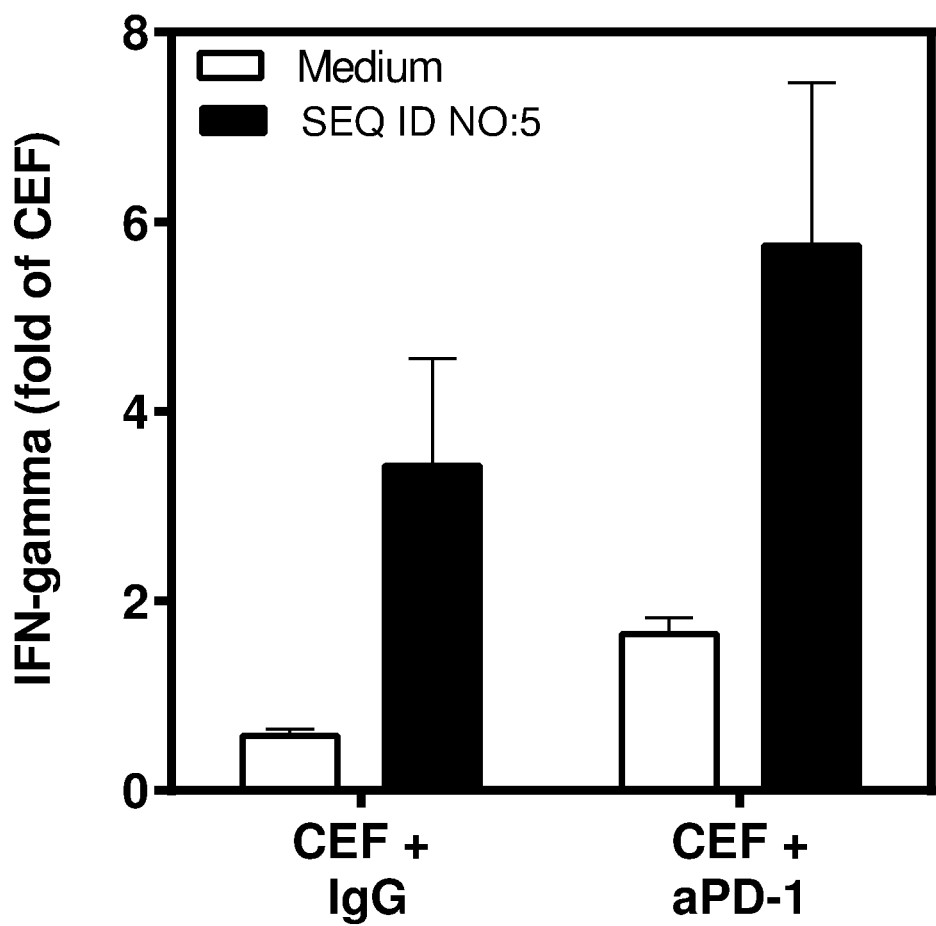
FIG. 2 In vitro stimulation of human PBMC with peptides selected from HLA class I-restricted T-cell epitopes of recall-antigens.

The synergistic combinatory effect of SEQ ID NO:5 with anti-PD-1 shown in FIG. 1A, B was confirmed in vitro when human peripheral blood mononuclear cells (PBMC) were incubated with antigenic peptides and a combination of SEQ ID NO:5 and anti-PD-1. Peptides were selected from HLA class-I-restricted T-cell epitopes of recall antigens (CMV, EBV, Flu=CEF) and the combination with SEQ ID NO:5 clearly increased the INF-gamma secretion by the PBMC compared to injection of SEQ ID NO:5 or anti-PD-1 alone (FIG. 2). The final concentration of the peptides was 1 µg/ml per peptide, SEQ ID NO:5 was used in a concentration of 3 µM and anti-PD-1 with 10 µg/ml (n=4). IFN-gamma secretion was analyzed as a marker for immune response; normalized to IFN-gamma level after stimulation of PBMC with CEF-peptides alone. Murine IgG (10 µg/ml) was used as control for anti-PD-1.

Figure 3A:
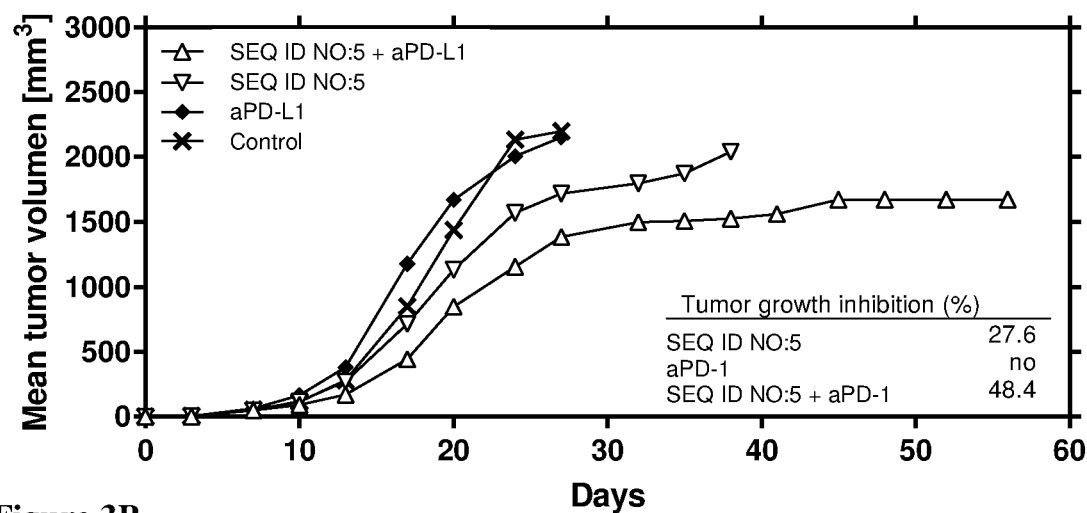
FIG. 3A, B Anti-tumor activity of the combination of SEQ ID NO:5 with anti-PD-L1.
Figure 3B:
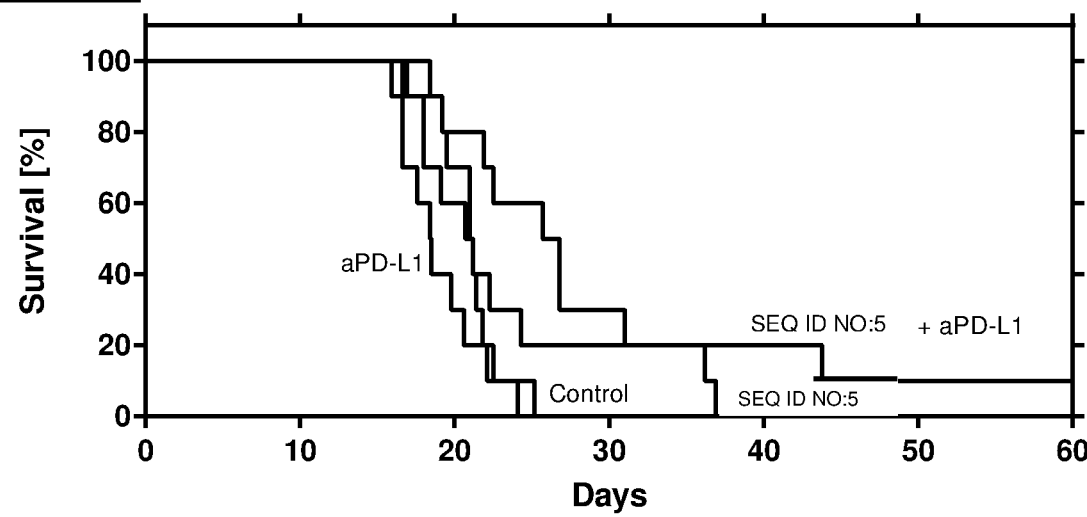

Furthermore, in a mouse CT26 tumor model, the surprising beneficial effects of the combination therapy of anti-PD-L1 and SEQ ID NO:5 was also clearly superior to the either SEQ ID NO:5 or anti-PD-L1 monotherapy. Tumor growth was reduced (FIG. 3A) and survival was augmented (FIG. 3B). 10 mice per group were inoculated s.c. with CT26 murine tumor cells and injected with SEQ ID NO:5 (250 µg/application, s.c. on day 3, 5, 7, 10, 12, 14, 17, 19, 21, 24, and 26), anti-PD-L1 (10 mg/kg per application, i.p. on day 3, 5, 7, 9, 11, 13, 15, 17), or both. Injection of vehicle (s.c.) served as control. FIG. 3A shows mean tumor growth—inlay, mean tumor growth inhibition from day 17 to 27 (at day 20: 23.0% for lefitolimod, no inhibition for anti-PD-L1, 39.9% for the combination). FIG. 1B shows a Kaplan-Meier survival plot.

The combinatorial effect of applying SEQ ID NO:6 having the loop sequence TCATCGTCGTTTTGTCGTTTTGTCGTTCTT was also investigated.

Figure 4A:
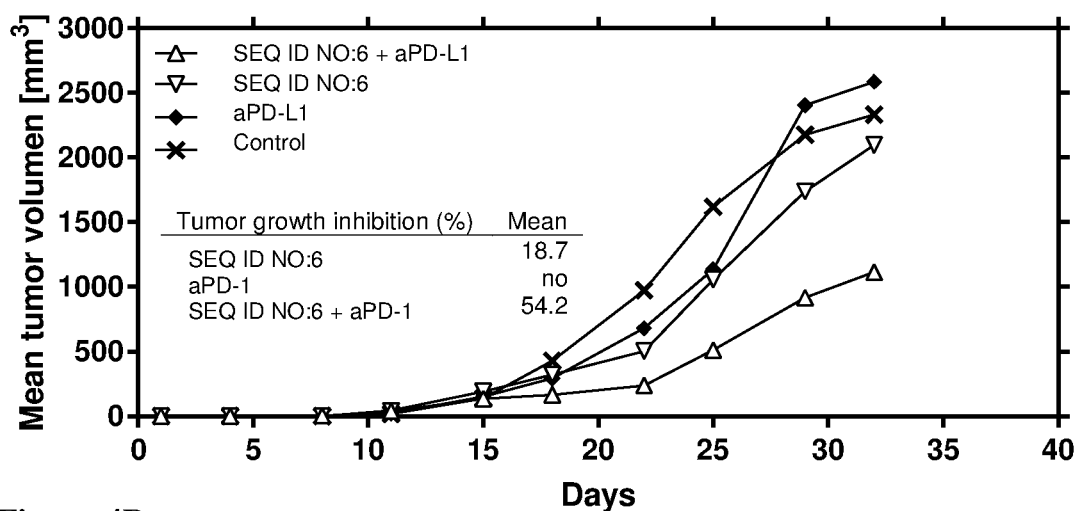
FIG. 4A, B Anti-tumor activity of the combination of SEQ ID NO:6 with anti-PD-1.

SEQ ID NO:6 was administered together with anti-PD-1 in a mouse CT26 tumor model. This combination surprisingly profoundly augmented the anti-tumor effect compared to the monotherapy with the single agents, SEQ ID NO:6 or anti-PD-1 (FIG. 4A, B). Again, 10 mice per group were inoculated s.c. with CT26 murine tumor cells and injected with SEQ ID NO:6 (250 µg/application, i.tu. on day 15, 17, 19, 22, 24, 26, 29, 31), anti-PD-1 (100 µg/application, i.p. on day 3, 6, 10 and 13), or both. Injection of vehicle (i.tu.) served as control. FIG. 4A shows the mean tumor growth—inlay, mean tumor growth inhibition from day 15 to 29 (at day 23: 48.2% for SEQ ID NO:6, no inhibition for anti-PD-1, 75.4 for the combination). FIG. 1B shows a mean Kaplan-Meier survival plot.

Figure 4B:
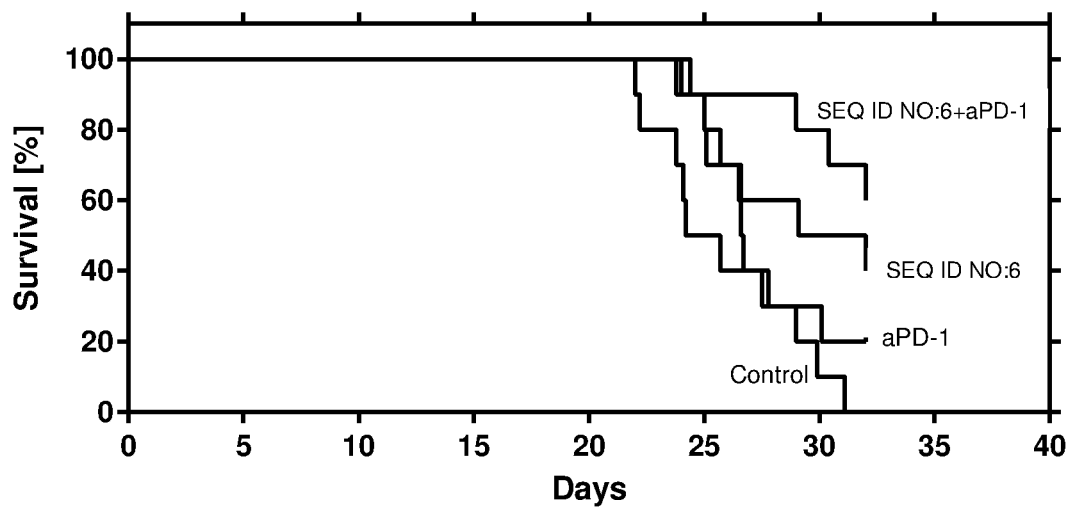
Figure 5:
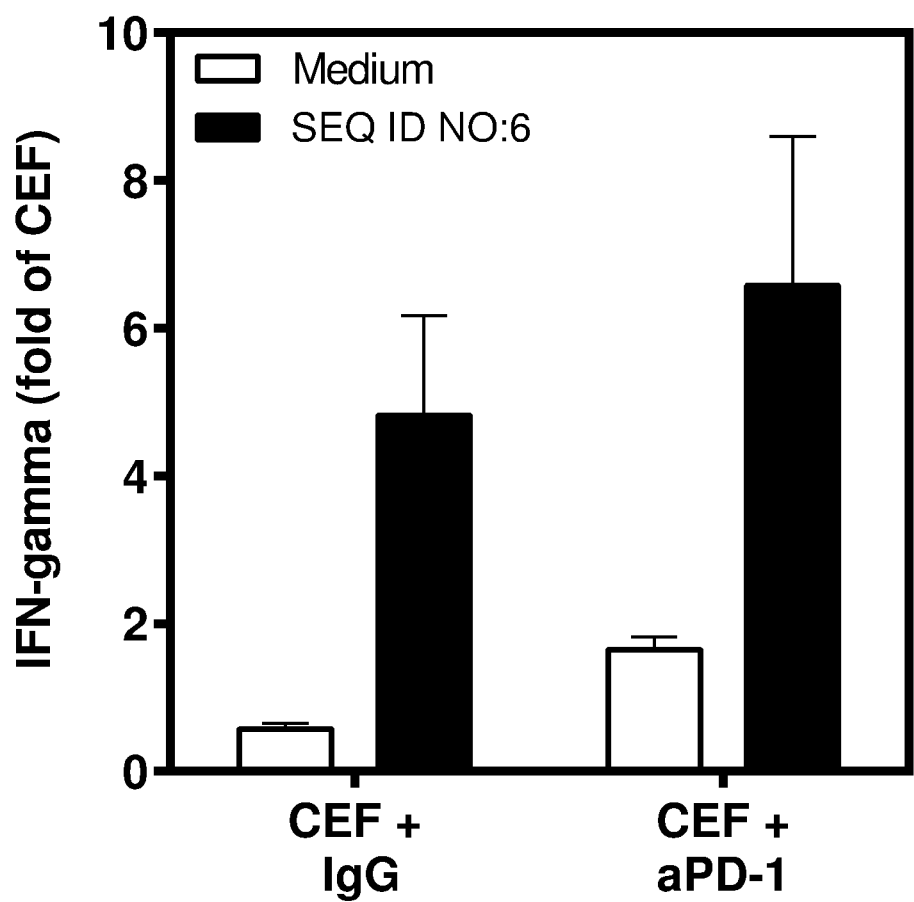
FIG. 5 In vitro stimulation of human PBMC with peptides selected from HLA class I-restricted T-cell epitopes of recall-antigens, SEQ ID NO:6 and anti-PD-.

The results shown in FIG. 4 are in line with the in vitro stimulation data of human PBMC with antigenic peptides, also showing surprisingly a benefit of the combination over the single use of the compounds (FIG. 5). Peptides selected from HLA class I-restricted T-cell epitopes of recall-antigens (CMV, EBV, Flu=CEF) with a final concentration of 1 µg/ml per peptide, SEQ ID NO:6 in a concentration of 3 µM and anti-PD-1 with 10 µg/ml (n=4) were used. IFN-gamma secretion was used as a marker for immune response; normalized to IFN-gamma level after stimulation of PMBC with CEF-peptides alone. Murine IgG (10 µg/ml) was used as control for anti-PD-1.

Oligos comprising nucleotides in L-conformation were used in further studies. Those oligos comprise L-nucleotides at indicated positions. DNA molecules were used with the core sequence [yTCATTxCGTGACGTGACGTTCzv] (y=2 to 8 G, protected with 1 to 3 L-deoxyribose or not; x=3 to 4 A; z=2 to 6 T protected with 1 to 3 L-deoxyribose; v=A, G, C, T).

These L-nucleotide comprising molecules showed increased immune modulatory and anti-tumor properties when combined with checkpoint inhibitors. For instance, combination of SEQ ID NO:7 (GGGGTCATT AAAACGTGACGTGACGTTCTTTTT, L-deoxyribose containing bases underlined) with anti-CTLA-4 in a mouse CT26 tumor model resulted in a surprisingly efficient decreased tumor growth compared to SEQ ID NO:7 or anti-CTLA-4 monotherapy (FIG. 6). 10 mice per group were inoculated s.c. with CT26 murine tumor cells and injected with SEQ ID NO:7 (200 µg/application, s.c. on day 3, 5, 8, 10, 12, 15, 17, 19, 22, 14 and 26), anti-CTLA-4 (100 µg/application at day 8; 50 µg/application at day 11 and 14, i.p.), or both. Injection of vehicle (s.c.) served as control. FIG. 6A shows the mean tumor growth—inlay, mean tumor growth inhibition from day 15 to 30 (at day 22: 19.8% for SEQ ID NO:7, 59.1% for anti-PD-1, 65.3% for the combination). FIG. 6B shows a Kaplan-Meier survival plot.

Figure 7A:
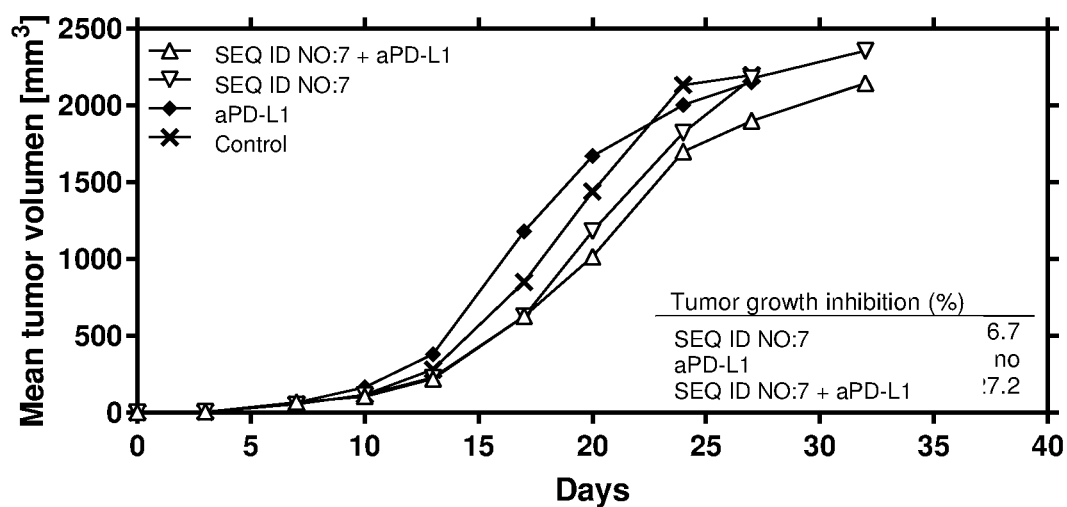
FIG. 7A, B Anti-tumor activity of the combination of SEQ ID NO:7 with anti-PD-L1.
Figure 7B:
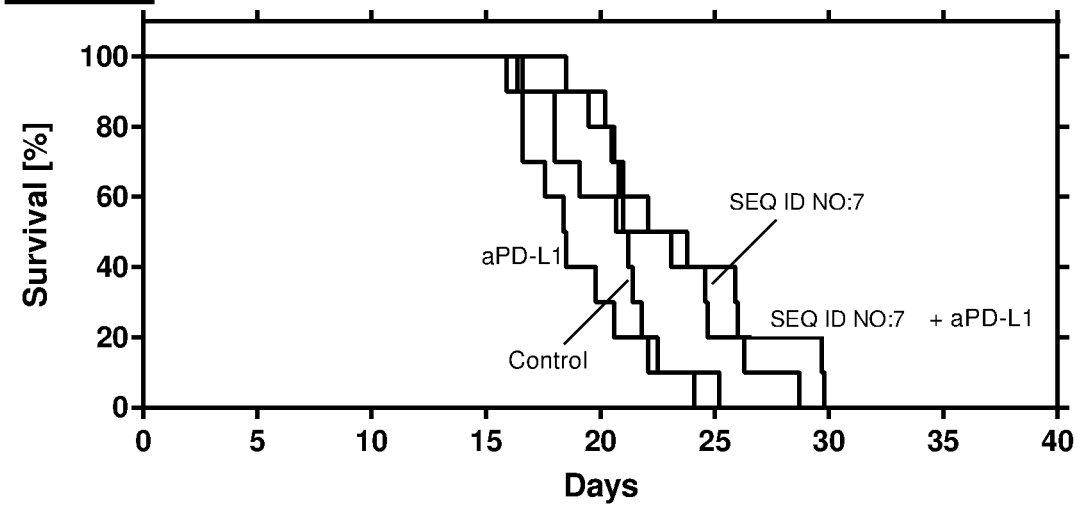

The combination of SEQ ID NO:7 with anti-PD-L1 also showed a moderately increased anti-tumor effect compared to that of the single compounds SEQ ID NO:7 or anti-PD-L1 in the mouse CT26 tumor model (FIG. 7). 10 mice per group were inoculated s.c. with CT26 murine tumor cells and injected with SEQ ID NO:7 (s.c. on day 3, 5, 7, 10, 12, 14, 17, 19, 21, 24, and 26), anti-PD-L1 (10 mg/kg per application, i.p. on day 3, 5, 7, 9, 11, 13, 15, 17), or both. Injection of vehicle (s.c.) served as control. FIG. 7A shows the mean tumor growth—inlay, mean tumor growth inhibition from day 13 to 27 (at day 20: 16.3% for SEQ ID NO:7, no inhibition for anti-PD-L1, 33.3% for the combination). FIG. 7B shows a Kaplan-Meier survival plot.

Figure 8A:
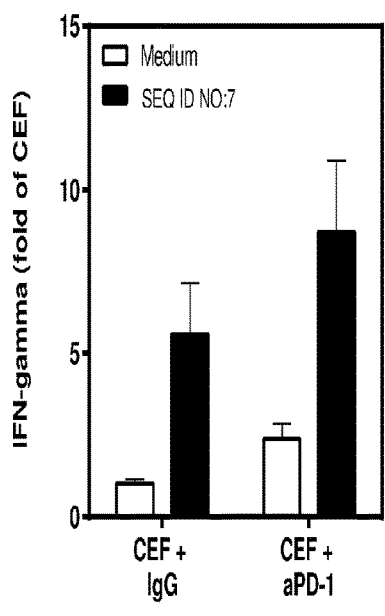
FIG. 8A-C In vitro stimulation of human PBMC with peptides selected from HLA class I-restricted T-cell epitopes of recall-antigens, SEQ ID NO:9 and anti-PD-.
Figure 8B:
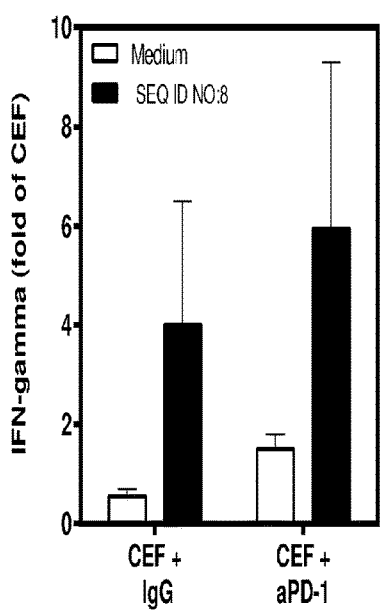
Figure 8C:
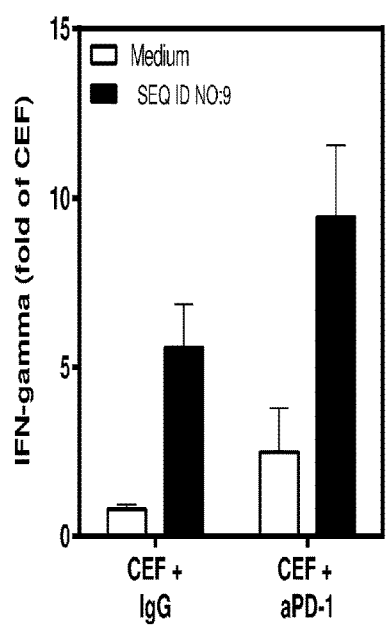

In in vitro studies the benefit of the combination of anti-PD-1 with SEQ ID NO:7, SEQ ID NO:8 (GGGGGGGGTCAT-TAAAACGTGACGTGACGTTCTTTTT, L-deoxyribose containing bases underlined), and SEQ ID NO:9 (GGGGT-CATTAAACGTGACGTGA CGTTCTTTTT, L-deoxyribose containing bases underlined) was observed regarding IFN-gamma secretion from PBMC stimulated with antigenic peptides (FIG. 8). Peptides were selected from HLA class I-restricted T-cell epitopes of recall-antigens (CMV, EBV, Flu=CEF; final concentration 1 µg/ml per peptide), SEQ ID NO:7 (A, n=12), SEQ ID NO:8 (B, n=2), SEQ ID NO:9 (C, n=4), each DNA molecule at a final concentration of 3 µM; and anti-PD-1 (10 µg/ml). Analysis of IFN-gamma secretion as marker for immune response; normalized to IFN-gamma level after stimulation with CEF-peptides alone. Murine IgG (10 µg/ml) was used as control for anti-PD-1

In another series of experiments DNA molecules with the core sequence [yTCATTxCGTTCTTCGGGGCGTTCzv] (y=2 to 8 G, protected with 1 to 3 L-deoxyribose or not; x=3 to 4 A; z=2 to 6 T protected with 1 to 3 L-deoxyribose; v=A, G, C, T) were used.

The combinatory effect regarding immunomodulation and anti-tumor effect was established for this group as well. As example for this group, SEQ ID NO:10 (GGGGTCAT-TAAACGTTCTTCGGGG CGTTCTTTTT, L-deoxyribose containing bases underlined) was used to investigate the combination with anti-PD-1.

Figure 9A:
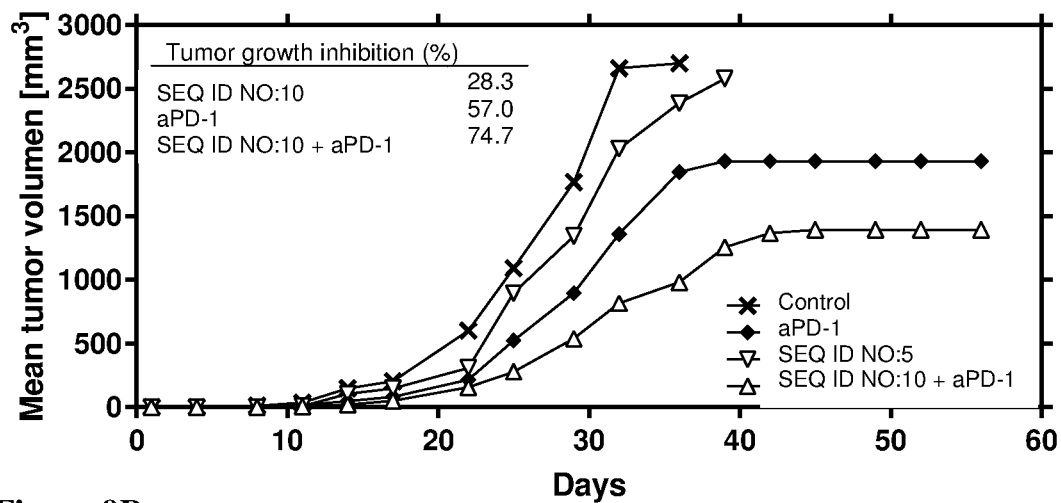
FIG. 9A, B Anti-tumor activity of the combination of SEQ ID NO:10 with anti-PD-1.
Figure 9B:
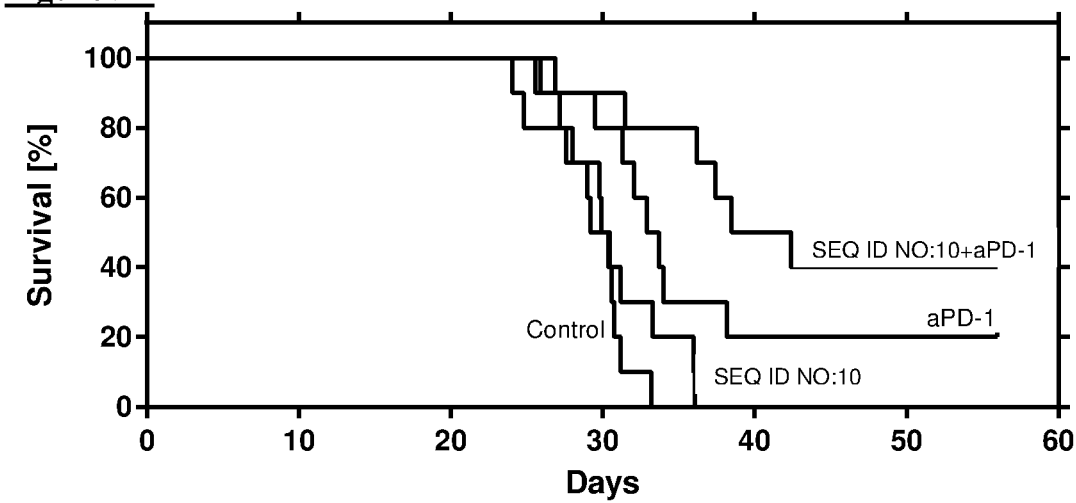

The combination resulted in a profound reduction of the tumor growth in a mouse CT26 tumor model (FIG. 9). 10 mice per group were inoculated s.c. with CT26 murine tumor cells and injected with SEQ ID NO:10 (200 µg/application, s.c. on day 3, 5, 8, 10, 12, 15, 17, 19, 22, 14 and 26), anti-PD-1 (200 µg/application, i.p. on day 3, 6, 10 and 14), or both. Injection of vehicle (s.c.) served as control. FIG. 9A shows the mean tumor growth—inlay, mean tumor growth inhibition from day 14 to 32 (at day 25: 17.8% for SEQ ID NO:10, 51.9% for anti-PD-1, 74.6% for the combination). FIG. 9B shows a Kaplan-Meier survival plot.

Figure 10A:
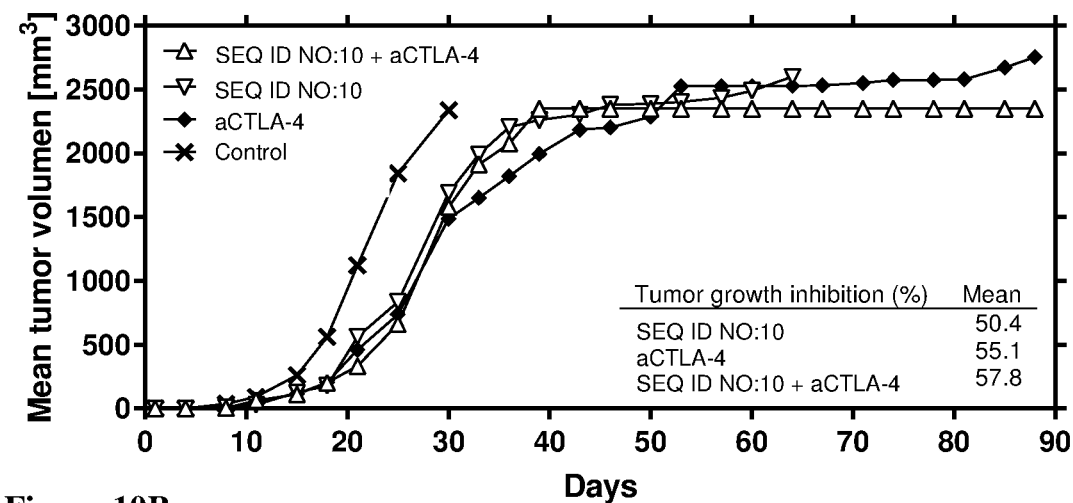
FIG. 10A, B Anti-tumor activity of the combination of SEQ ID NO:10 with anti-CTLA-4.
Figure 10B:
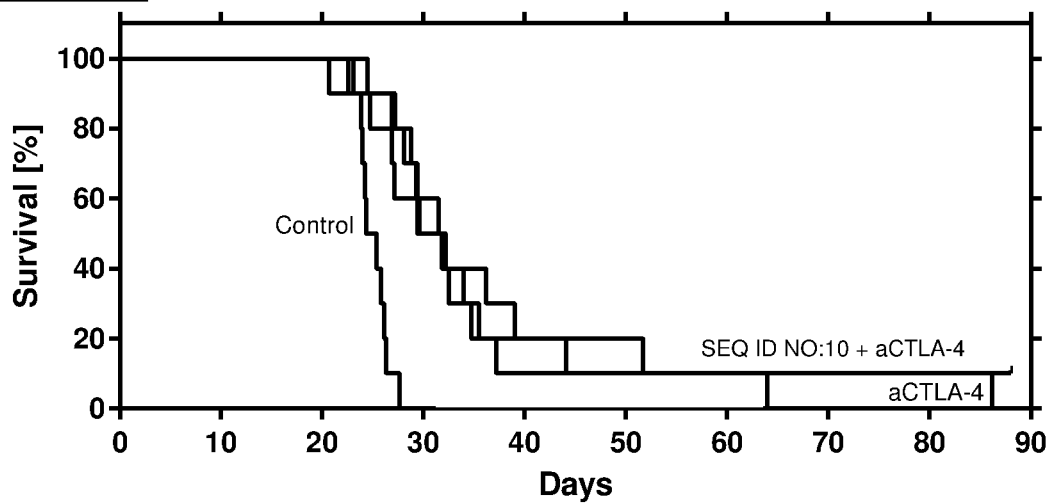

In addition, a combination of SEQ ID NO:10 with anti-CTLA-4 lead to a decreased tumor growth in mouse CT26 tumor model compared to treatment with the single agents, SEQ ID NO:10 or anti-CTLA-4 (FIG. 10). 10 mice per group were inoculated s.c. with CT26 murine tumor cells and injected with SEQ ID NO:10 (200 µg/application, s.c. on day 3, 5, 8, 10, 12, 15, 17, 19, 22, 14 and 26), anti-CTLA-4 (100 µg/application at day 8, 50 µg/application at day 11 and 14, i.p.), or both. Injection of vehicle (s.c.) served as control. FIG. 10A shows the mean tumor growth—inlay, mean tumor growth inhibition from day 15 to 30 (at day 22: 49.7% for SEQ ID NO:10, 59.1% for anti-PD-1, 70.3% for the combination). FIG. 10B shows a Kaplan-Meier survival plot.

Figure 11:
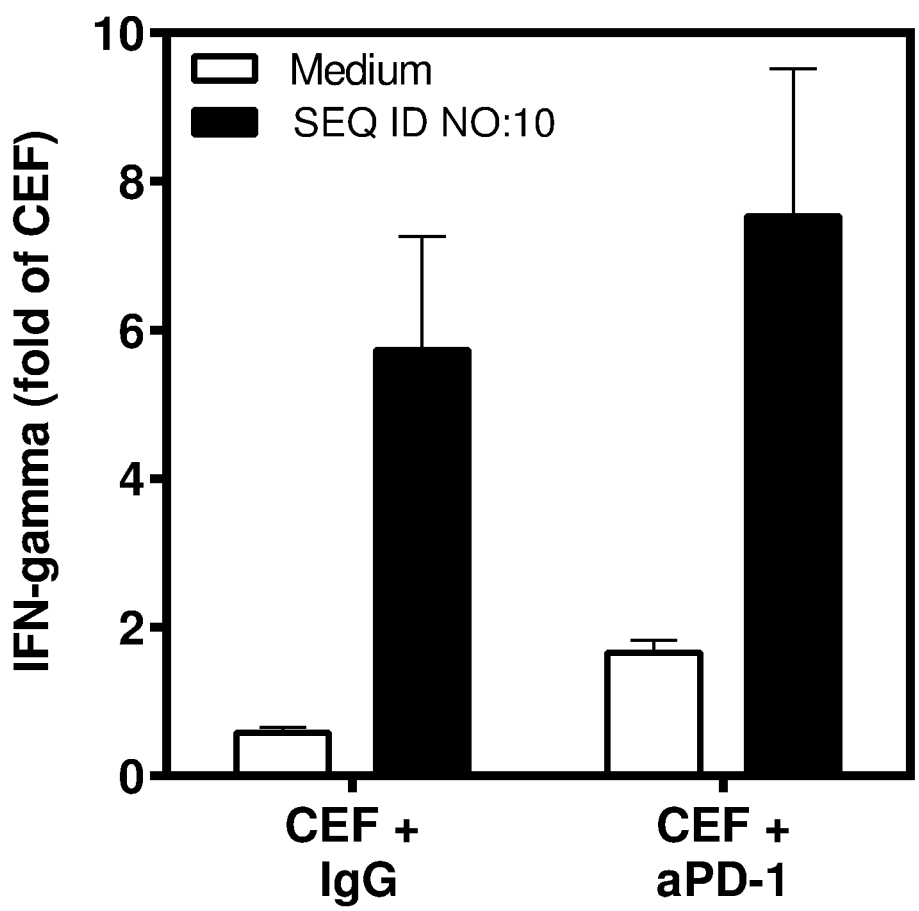
FIG. 11 In vitro stimulation of human PBMC with peptides selected from HLA class I-restricted T-cell epitopes of recall-antigens, SEQ ID NO:10 and anti-PD-.

Furthermore, a combination of SEQ ID NO:10 and anti-PD-1 was evaluated in in vitro PBMC stimulation studies and showed an increased effect regarding IFN-gamma secretion compared to SEQ ID NO:10 or anti-PD-1 alone (FIG. 11). Peptides were selected from HLA class I-restricted T-cell epitopes of recall-antigens (CMV, EBV, Flu=CEF; final concentration 1 µg/ml per peptide)), SEQ ID NO:10 (3 µM) and anti-PD-1 (10 µg/ml) (n=5). Analysis of IFN-gamma secretion served as marker for an immune response; normalized to IFN-gamma level after stimulation with CEF-peptides alone. Murine IgG (10 µg/ml) was used as control for anti-PD-1.

In a further experiment, a DNA molecule with a core sequence [yTCATTxTCGTCGTTTTGTCGTTTTGTCGzv] (y=2 to 8 G, protected with 1 to 3 L-deoxyribose or not; x=3 to 4 A; z=2 to 6 T protected with 1 to 3 L-deoxyribose; v=A, G, C, T) was used in experiments.

Figure 12:
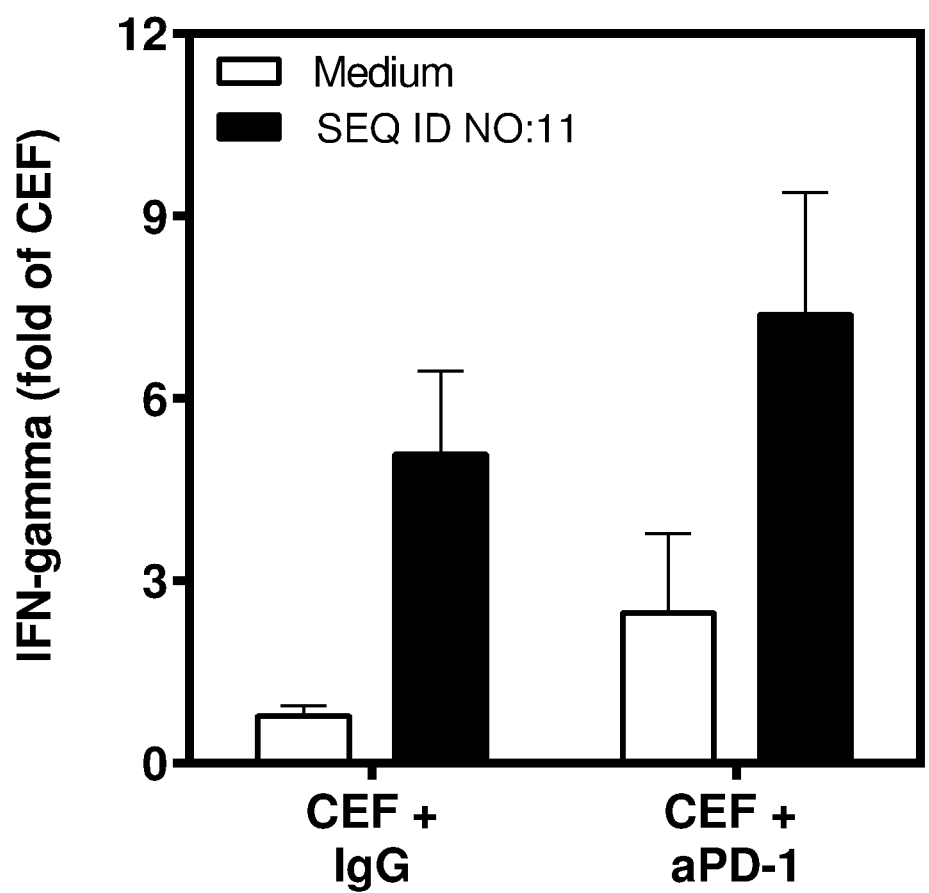
FIG. 12 In vitro stimulation of human PBMC with peptides selected from HLA class I-restricted T-cell epitopes of recall-antigens, SEQ ID NO:11 and anti-PD-1.

SEQ ID NO:11 (GGGGTCAT-TAAATCGTCGTTTTGTCGTTTTGTCGTTTTT, L-deoxyribose containing bases underlined) was used as example for this group. When SEQ ID NO:11 was combined with anti-PD-1 in vitro in PBMC studies,—IFN-gamma secretion surprisingly significantly increased showing an improvement compared to SEQ ID NO:11 or anti-PD-1 alone (FIG. 12). Peptides selected from HLA class I-restricted T-cell epitopes of recall-antigens (CMV, EBV, Flu=CEF; final concentration 1 µg/ml per peptide), SEQ ID NO:11 (3 µM) and anti-PD-1 (10 µg/ml) (n=4). Analysis of IFN-gamma secretion as marker for immune response; normalized to IFN-gamma level after stimulation with CEF-peptides alone. Murine IgG (10 µg/ml) was used as control for aPD-1.

Finally, a DNA molecules with the core sequence [yAC-GATCGTCwT] (y=2 to 8 G, protected with 1 to 3 L-deoxyribose or not; w=4 to 12 G protected with 1 to 3 L-deoxyribose) was used for testing effects of combinatorial application.

Figure 13:
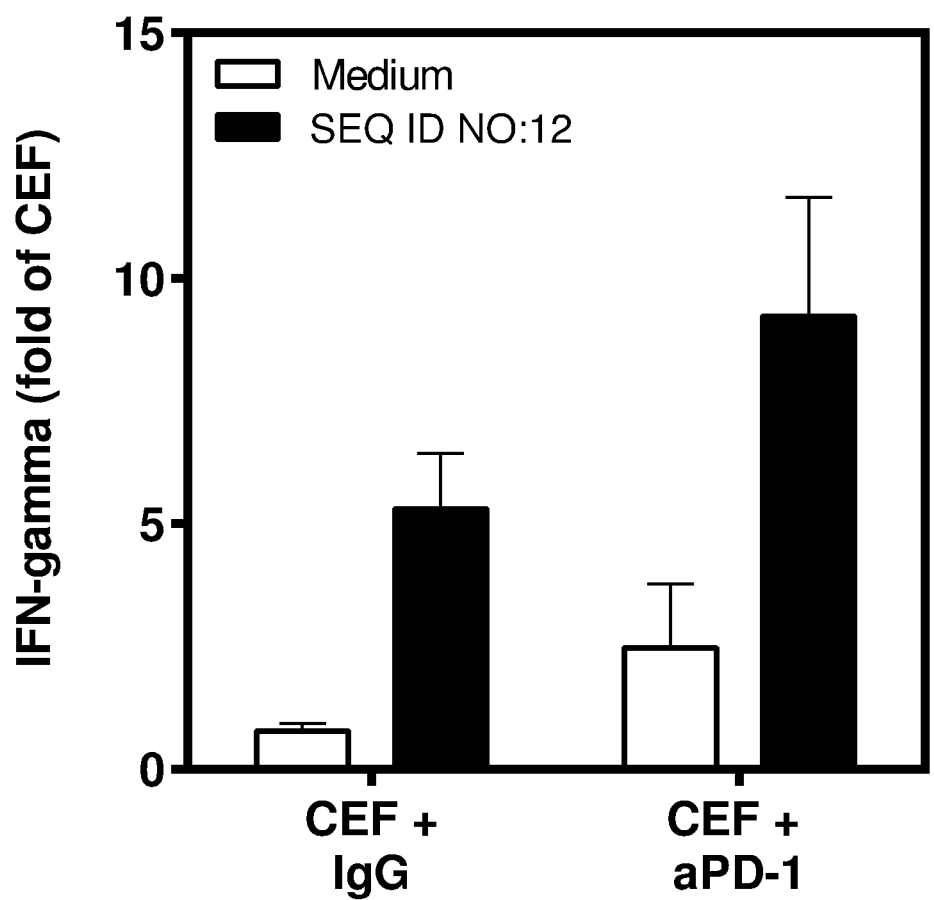
FIG. 13 In vitro stimulation of human PBMC with peptides selected from HLA class I-restricted T-cell epitopes of recall-antigens, EnanDIM362 and anti-PD-1.

An example for this group is SEQ ID NO:12 (GGGGGACGATCGTCGGGGGGT, L-deoxyribose containing bases underlined). In in vitro stimulation studies with human PBMC its combination with anti-PD-1 was evaluated leading to a significantly augmented immune response compared to the single compounds (FIG. 13). Peptides were selected from HLA class I-restricted T-cell epitopes of recall-antigens (CMV, EBV, Flu=CEF; final concentration 1 µg/ml per peptide), SEQ ID NO:12 (3 µM) and anti-PD-1 (10 µg/ml) (n=4). Analysis of IFN-gamma secretion as marker for immune response; normalized to IFN-gamma level after stimulation with CEF-peptides alone. Murine IgG (10 µg/ml) was used as control for aPD-1.

Taking the above described experimental settings into account and a weight of a mouse of about 20 g, the amounts of DNA to be applied lies in a range of about 12.5 mg/kg weight, so that it seems to be feasible that maximal 15 mg/kg will be necessary for obtaining the shown surprising results.

Anti-PD-1 antibody has been applied with 10 mg/kg weight so that the application of maximal 15 mg/kg weight also seems to be necessary for obtaining the shown surprising results.

The invention claimed is:

1. A linear open-chained non-coding sequence of deoxyribonucleic acids selected from SEQ ID NO: 7, SEQ ID NO: 8 and SEQ ID NO: 9.

2. The linear open-chained non-coding sequence of claim 1, consisting of SEQ ID NO: 7.

3. The linear open-chained non-coding sequence of claim 1, consisting of SEQ ID NO: 8.

4. The linear open-chained non-coding sequence of claim 1, consisting of SEQ ID NO: 9.

* * * * *